United States Patent
Koss

(10) Patent No.: US 10,004,555 B2
(45) Date of Patent: *Jun. 26, 2018

(54) ELECTROSURGICAL TISSUE DISSECTING DEVICE

(71) Applicant: Aesculap AG, Tuttlingen (DE)

(72) Inventor: Timothy A. Koss, Discovery Bay, CA (US)

(73) Assignee: Aesculap AG, Tuttlingen (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/094,332

(22) Filed: Apr. 8, 2016

(65) Prior Publication Data

US 2016/0242840 A1  Aug. 25, 2016

Related U.S. Application Data

(63) Continuation of application No. 13/536,149, filed on Jun. 28, 2012, now Pat. No. 9,339,327.

(60) Provisional application No. 61/502,268, filed on Jun. 28, 2011.

(51) Int. Cl.
  *A61B 18/14* (2006.01)
  *A61B 18/00* (2006.01)

(52) U.S. Cl.
  CPC .. *A61B 18/1445* (2013.01); *A61B 2018/0063* (2013.01); *A61B 2018/00601* (2013.01); *A61B 2018/1412* (2013.01); *A61B 2018/1452* (2013.01)

(58) Field of Classification Search
  CPC ............ A61B 18/1442; A61B 18/1445; A61B 2018/00077; A61B 2018/00083
  See application file for complete search history.

(56) References Cited

U.S. PATENT DOCUMENTS

| | | |
|---|---|---|
| 1,918,700 A | 7/1933 | Harris |
| 3,356,408 A | 12/1967 | Stutz |
| 3,527,224 A | 9/1970 | Rabinowitz |
| 3,709,215 A | 1/1973 | Richmond |
| 3,742,955 A | 7/1973 | Battista |
| 3,845,771 A | 11/1974 | Vise |
| 3,920,021 A | 11/1975 | Hiltebrandt |
| 3,970,088 A | 7/1976 | Morrison |
| 4,018,230 A | 4/1977 | Ochiai |

(Continued)

FOREIGN PATENT DOCUMENTS

| | | |
|---|---|---|
| CA | 2061215 | 2/1992 |
| CN | 1250360 | 4/2000 |

(Continued)

OTHER PUBLICATIONS

Entire patent prosecution history of U.S. Appl. No. 13/536,149, filed Jun. 28, 2012, entitled, "Electrosurgical Tissue Dissecting Device."

(Continued)

*Primary Examiner* — Joseph Dietrich
(74) *Attorney, Agent, or Firm* — RatnerPrestia

(57) ABSTRACT

Electrosurgical devices, methods, and systems for electrosurgical procedures as enabled by bipolar radiofrequency energy. An electrosurgical tissue dissecting device includes a shaft, a distally directed member that extends in a distal direction from the shaft, a first electrode that either forms part of or is positioned on the distally directed member, and a second electrode that is movable with respect to the first electrode.

12 Claims, 8 Drawing Sheets

(56) References Cited

U.S. PATENT DOCUMENTS

| | | |
|---|---|---|
| 4,041,952 A | 8/1977 | Morrison, Jr. |
| 4,072,153 A | 2/1978 | Swartz |
| 4,094,320 A | 6/1978 | Newton |
| 4,231,372 A | 11/1980 | Newton |
| 4,492,231 A | 1/1985 | Auth |
| 4,532,924 A | 8/1985 | Auth |
| 4,590,934 A | 5/1986 | Malis |
| 4,644,953 A | 2/1987 | Lahodny |
| 4,671,274 A | 6/1987 | Sorochenko |
| 4,972,846 A | 11/1990 | Owens |
| 4,976,717 A | 12/1990 | Boyle |
| 4,979,948 A | 12/1990 | Geddes |
| 4,998,527 A | 3/1991 | Meyer |
| 5,037,379 A | 8/1991 | Clayman |
| 5,041,101 A | 8/1991 | Seder |
| 5,059,782 A | 10/1991 | Fukuyama |
| 5,078,736 A | 1/1992 | Behl |
| 5,108,408 A | 4/1992 | Lally |
| 5,133,713 A | 7/1992 | Huang |
| 5,151,102 A | 9/1992 | Kamiyama |
| 5,156,613 A | 10/1992 | Sawyer |
| 5,178,618 A | 1/1993 | Kandarpa |
| 5,190,541 A | 3/1993 | Abele |
| 5,207,691 A | 5/1993 | Nardella |
| 5,217,030 A | 6/1993 | Yoon |
| 5,234,425 A | 8/1993 | Fogarty |
| 5,250,074 A | 10/1993 | Wilk |
| 5,267,998 A | 12/1993 | Hagen |
| 5,269,780 A | 12/1993 | Roos |
| 5,269,782 A | 12/1993 | Sutter |
| 5,273,524 A | 12/1993 | Fox |
| 5,277,201 A | 1/1994 | Stern |
| 5,281,216 A | 1/1994 | Klicek |
| 5,282,799 A | 2/1994 | Rydell |
| 5,290,287 A | 3/1994 | Boebel |
| 5,295,990 A | 3/1994 | Levin |
| 5,300,068 A | 4/1994 | Rosar |
| 5,300,087 A | 4/1994 | Knoepfler |
| 5,312,023 A | 5/1994 | Green |
| 5,324,289 A | 6/1994 | Eggers |
| 5,330,471 A | 7/1994 | Eggers |
| 5,330,502 A | 7/1994 | Hassler |
| 5,336,229 A | 8/1994 | Noda |
| 5,336,237 A | 8/1994 | Chin |
| 5,341,807 A | 8/1994 | Nardella |
| 5,342,381 A | 8/1994 | Tidemand |
| 5,352,223 A | 10/1994 | McBrayer |
| 5,352,235 A | 10/1994 | Koros |
| 5,354,336 A | 10/1994 | Kelman |
| 5,356,408 A | 10/1994 | Rydell |
| 5,366,477 A | 11/1994 | LeMarie, III |
| 5,374,277 A | 12/1994 | Hassler |
| 5,377,415 A | 1/1995 | Gibson |
| 5,391,166 A | 2/1995 | Eggers |
| 5,395,369 A | 3/1995 | McBrayer |
| 5,395,375 A | 3/1995 | Turkel |
| 5,396,900 A | 3/1995 | Slater |
| 5,397,320 A | 3/1995 | Essig |
| 5,403,312 A | 4/1995 | Yates |
| 5,417,687 A | 5/1995 | Nardella |
| 5,423,814 A | 6/1995 | Zhu |
| 5,431,676 A | 7/1995 | Dubrul |
| 5,438,302 A | 8/1995 | Goble |
| 5,443,463 A | 8/1995 | Stern |
| 5,443,470 A | 8/1995 | Stern |
| 5,445,638 A | 8/1995 | Rydell |
| 5,447,513 A | 9/1995 | Davison |
| 5,449,355 A | 9/1995 | Rhum |
| 5,456,684 A | 10/1995 | Schmidt |
| 5,458,598 A | 10/1995 | Feinberg |
| 5,462,546 A | 10/1995 | Rydell |
| 5,472,442 A | 12/1995 | Klicek |
| 5,480,399 A | 1/1996 | Hebborn |
| 5,482,054 A | 1/1996 | Slater |
| 5,484,435 A | 1/1996 | Fleenor |
| 5,484,436 A | 1/1996 | Eggers |
| 5,496,312 A | 3/1996 | Klicek |
| 5,496,317 A | 3/1996 | Goble |
| 5,514,134 A | 5/1996 | Rydell |
| 5,520,698 A | 5/1996 | Koh |
| 5,531,744 A | 7/1996 | Nardella |
| 5,540,684 A | 7/1996 | Hassler, Jr. |
| 5,540,685 A | 7/1996 | Parins |
| 5,542,945 A | 8/1996 | Fritzsch |
| 5,549,637 A | 8/1996 | Crainich |
| 5,556,397 A | 9/1996 | Long |
| 5,558,100 A | 9/1996 | Cox |
| 5,558,671 A | 9/1996 | Yates |
| 5,562,700 A | 10/1996 | Huitema |
| 5,562,701 A | 10/1996 | Huitema |
| 5,562,702 A | 10/1996 | Huitema |
| 5,562,720 A | 10/1996 | Stern |
| 5,569,243 A | 10/1996 | Kortenbach |
| 5,571,100 A | 11/1996 | Goble |
| 5,573,535 A | 11/1996 | Viklund |
| 5,578,052 A | 11/1996 | Koros |
| 5,599,350 A | 2/1997 | Schulze |
| 5,601,224 A | 2/1997 | Bishop |
| 5,603,700 A | 2/1997 | Daneshvar |
| 5,603,711 A | 2/1997 | Parins |
| 5,611,803 A | 3/1997 | Heaven |
| 5,624,452 A | 4/1997 | Yates |
| 5,637,110 A | 6/1997 | Pennybacker |
| 5,637,111 A | 6/1997 | Sutcu |
| 5,653,692 A | 8/1997 | Masterson |
| 5,658,281 A | 8/1997 | Heard |
| 5,662,662 A | 9/1997 | Bishop |
| 5,662,676 A | 9/1997 | Koninckx |
| 5,665,085 A | 9/1997 | Nardella |
| 5,665,100 A | 9/1997 | Yoon |
| 5,667,526 A | 9/1997 | Levin |
| 5,669,907 A | 9/1997 | Platt, Jr. |
| 5,673,840 A | 10/1997 | Schulze |
| 5,673,841 A | 10/1997 | Schulze |
| 5,674,184 A | 10/1997 | Hassler, Jr. |
| 5,674,220 A | 10/1997 | Fox |
| 5,675,184 A | 10/1997 | Matsubayashi |
| 5,680,982 A | 10/1997 | Schulze |
| 5,681,282 A | 10/1997 | Eggers |
| 5,683,385 A | 11/1997 | Kortenbach |
| 5,683,388 A | 11/1997 | Slater |
| 5,688,270 A | 11/1997 | Yates |
| 5,693,051 A | 12/1997 | Schulze |
| 5,697,949 A | 12/1997 | Giurtino |
| 5,700,261 A | 12/1997 | Brinkerhoff |
| 5,702,390 A | 12/1997 | Austin |
| 5,704,534 A | 1/1998 | Huitema |
| 5,707,369 A | 1/1998 | Vaitekunas |
| 5,709,680 A | 1/1998 | Yates |
| 5,713,896 A | 2/1998 | Nardella |
| 5,715,832 A | 2/1998 | Koblish |
| 5,718,703 A | 2/1998 | Chin |
| 5,720,719 A | 2/1998 | Edwards |
| 5,728,143 A | 3/1998 | Gough |
| 5,733,283 A | 3/1998 | Malis |
| 5,735,289 A | 4/1998 | Pfeffer |
| 5,735,848 A | 4/1998 | Yates |
| 5,735,849 A | 4/1998 | Baden |
| 5,741,285 A | 4/1998 | McBrayer |
| 5,746,750 A | 5/1998 | Prestel |
| 5,749,895 A | 5/1998 | Sawyer |
| 5,755,717 A | 5/1998 | Yates |
| 5,776,130 A | 7/1998 | Buysse |
| 5,788,662 A | 8/1998 | Antanavich |
| 5,797,941 A | 8/1998 | Schulze |
| 5,810,811 A | 9/1998 | Yates |
| 5,817,091 A | 10/1998 | Nardella |
| 5,817,092 A | 10/1998 | Behl |
| 5,823,066 A | 10/1998 | Huitema |
| 5,833,689 A | 11/1998 | Long |
| 5,836,990 A | 11/1998 | Li |
| 5,840,077 A | 11/1998 | Rowden |
| 5,855,576 A | 1/1999 | LeVeen |
| 5,860,975 A | 1/1999 | Goble |

(56) References Cited

U.S. PATENT DOCUMENTS

| | | |
|---|---|---|
| 5,891,142 A | 4/1999 | Eggers |
| 5,893,835 A | 4/1999 | Witt |
| 5,893,874 A | 4/1999 | Bourque |
| 5,931,835 A | 8/1999 | Mackey |
| 5,931,836 A | 8/1999 | Hatta |
| 5,954,720 A | 9/1999 | Wilson |
| 5,976,128 A | 11/1999 | Schilling |
| 5,979,453 A | 11/1999 | Savage |
| 6,003,517 A | 12/1999 | Sheffield |
| 6,004,319 A | 12/1999 | Goble |
| 6,030,384 A | 2/2000 | Nezhat |
| 6,050,993 A | 4/2000 | Tu |
| 6,050,995 A | 4/2000 | Durgin |
| 6,056,744 A | 5/2000 | Edwards |
| 6,059,766 A | 5/2000 | Greff |
| 6,059,782 A | 5/2000 | Novak |
| 6,066,139 A | 5/2000 | Ryan |
| 6,068,626 A | 5/2000 | Harrington |
| 6,071,281 A | 6/2000 | Burnside |
| 6,074,386 A | 6/2000 | Goble |
| 6,086,586 A | 7/2000 | Hooven |
| 6,090,106 A | 7/2000 | Goble |
| 6,093,186 A | 7/2000 | Goble |
| 6,096,037 A | 8/2000 | Mulier |
| 6,099,550 A | 8/2000 | Yoon |
| 6,123,701 A | 9/2000 | Nezhat |
| H1904 H | 10/2000 | Yates |
| 6,142,992 A | 11/2000 | Cheng |
| 6,152,920 A | 11/2000 | Thompson |
| 6,152,932 A | 11/2000 | Ternstrom |
| 6,162,220 A | 12/2000 | Nezhat |
| 6,174,309 B1 | 1/2001 | Wrublewski |
| 6,179,832 B1 | 1/2001 | Jones |
| 6,203,541 B1 | 3/2001 | Keppel |
| 6,203,542 B1 | 3/2001 | Ellsberry |
| 6,206,877 B1 | 3/2001 | Kese |
| 6,210,406 B1 | 4/2001 | Webster |
| 6,212,426 B1 | 4/2001 | Swanson |
| 6,217,894 B1 | 4/2001 | Sawhney |
| 6,228,084 B1 | 5/2001 | Kirwan, Jr. |
| 6,234,178 B1 | 5/2001 | Goble |
| 6,241,139 B1 | 6/2001 | Milliman |
| 6,245,069 B1 | 6/2001 | Gminder |
| 6,254,601 B1 | 7/2001 | Burbank |
| 6,258,085 B1 | 7/2001 | Eggleston |
| 6,277,114 B1 | 8/2001 | Bullivant |
| 6,283,963 B1 | 9/2001 | Regula |
| 6,287,304 B1 | 9/2001 | Eggers |
| 6,290,715 B1 | 9/2001 | Sharkey |
| 6,293,942 B1 | 9/2001 | Goble |
| 6,293,946 B1 | 9/2001 | Thorne |
| 6,296,636 B1 | 10/2001 | Cheng |
| 6,312,430 B1 | 11/2001 | Wilson |
| 6,322,494 B1 | 11/2001 | Bullivant |
| 6,327,505 B1 | 12/2001 | Medhkour |
| 6,334,861 B1 | 1/2002 | Chandler |
| 6,350,274 B1 | 2/2002 | Li |
| 6,361,559 B1 | 3/2002 | Houser |
| 6,364,879 B1 | 4/2002 | Chen |
| 6,371,956 B1 | 4/2002 | Wilson |
| 6,391,024 B1 | 5/2002 | Sun |
| 6,391,029 B1 | 5/2002 | Hooven |
| 6,398,781 B1 | 6/2002 | Goble |
| 6,423,550 B1 | 6/2002 | Buysse |
| H2037 H | 7/2002 | Yates |
| 6,416,509 B1 | 7/2002 | Goble |
| 6,428,550 B1 | 8/2002 | Vargas |
| 6,436,096 B1 | 8/2002 | Hareyama |
| 6,464,702 B2 | 10/2002 | Schulze |
| 6,485,486 B1 | 11/2002 | Trembly |
| 6,485,489 B2 | 11/2002 | Teirstein |
| 6,491,690 B1 | 12/2002 | Goble |
| 6,494,881 B1 | 12/2002 | Bales |
| 6,500,176 B1 | 12/2002 | Truckai |
| 6,514,252 B2 | 2/2003 | Nezhat |
| 6,517,530 B1 | 2/2003 | Kleven |
| 6,520,185 B1 | 2/2003 | Bommannan |
| 6,533,784 B2 | 3/2003 | Truckai |
| 6,546,933 B1 | 4/2003 | Yoon |
| 6,554,829 B2 | 4/2003 | Schulze |
| 6,564,806 B1 | 5/2003 | Fogarty |
| 6,565,560 B1 | 5/2003 | Goble |
| 6,565,561 B1 | 5/2003 | Goble |
| 6,584,360 B2 | 6/2003 | Francischelii |
| 6,610,074 B2 | 8/2003 | Santilli |
| 6,616,654 B2 | 9/2003 | Mollenauer |
| 6,616,659 B1 | 9/2003 | delaTorre |
| 6,619,529 B2 | 9/2003 | Green |
| 6,623,482 B2 | 9/2003 | Pendekanti |
| 6,626,901 B1 | 9/2003 | Treat |
| 6,645,198 B1 | 11/2003 | Bommannan |
| 6,645,201 B1 | 11/2003 | Utley |
| 6,648,839 B2 | 11/2003 | Manna |
| 6,652,518 B2 | 11/2003 | Wellman |
| 6,656,177 B2 | 12/2003 | Truckai |
| 6,666,859 B1 | 12/2003 | Fleenor |
| 6,669,696 B2 | 12/2003 | Bacher et al. |
| 6,673,085 B1 | 1/2004 | Berg |
| 6,676,660 B2 | 1/2004 | Wamper |
| 6,682,526 B1 | 1/2004 | Jones |
| 6,682,527 B2 | 1/2004 | Strul |
| 6,695,840 B2 | 2/2004 | Schulze |
| 6,699,245 B2 | 3/2004 | Dinger |
| 6,719,754 B2 | 4/2004 | Underwood |
| 6,722,371 B1 | 4/2004 | Fogarty |
| 6,736,814 B2 | 5/2004 | Manna |
| 6,743,229 B2 | 6/2004 | Buysse |
| 6,746,488 B1 | 6/2004 | Bales |
| 6,752,154 B2 | 6/2004 | Fogarty |
| 6,752,803 B2 | 6/2004 | Goldman |
| 6,770,070 B1 | 8/2004 | Balbierz |
| 6,770,072 B1 | 8/2004 | Truckai |
| 6,808,525 B2 | 10/2004 | Latterell |
| 6,817,974 B2 | 11/2004 | Cooper |
| 6,821,273 B2 | 11/2004 | Mollenauer |
| 6,837,888 B2 | 1/2005 | Ciarrocca |
| 6,840,938 B1 | 1/2005 | Morley |
| 6,843,789 B2 | 1/2005 | Goble |
| 6,852,108 B2 | 2/2005 | Barry |
| 6,858,028 B2 | 2/2005 | Mulier |
| 6,889,089 B2 | 5/2005 | Behl |
| 6,893,435 B2 | 5/2005 | Goble |
| 6,896,672 B1 | 5/2005 | Eggers |
| 6,896,673 B2 | 5/2005 | Hooven |
| 6,905,497 B2 | 6/2005 | Truckai |
| 6,905,506 B2 | 6/2005 | Burbank |
| 6,913,579 B2 | 7/2005 | Truckai |
| 6,918,907 B2 | 7/2005 | Kelly |
| 6,918,909 B2 | 7/2005 | Ohyama |
| 6,923,803 B2 | 8/2005 | Goble |
| 6,926,712 B2 | 8/2005 | Phan |
| 6,929,642 B2 | 8/2005 | Xiao |
| 6,936,048 B2 | 8/2005 | Hurst |
| 6,939,346 B2 | 9/2005 | Kannenberg |
| 6,953,461 B2 | 10/2005 | McClurken |
| 6,981,628 B2 | 1/2006 | Wales |
| 7,011,657 B2 | 3/2006 | Truckai |
| 7,033,356 B2 | 4/2006 | Latterell |
| 7,063,699 B2 | 6/2006 | Hess |
| 7,090,637 B2 | 8/2006 | Danitz |
| 7,090,673 B2 | 8/2006 | Dycus |
| 7,090,685 B2 | 8/2006 | Kortenbach |
| 7,094,235 B2 | 8/2006 | Francischelli |
| 7,101,371 B2 | 9/2006 | Dycus |
| 7,101,372 B2 | 9/2006 | Dycus |
| 7,101,373 B2 | 9/2006 | Dycus |
| 7,118,587 B2 | 10/2006 | Dycus |
| 7,125,409 B2 | 10/2006 | Truckai |
| 7,137,980 B2 | 11/2006 | Buysse |
| 7,150,097 B2 | 12/2006 | Sremcich |
| 7,159,750 B2 | 1/2007 | Racenet |
| 7,166,102 B2 | 1/2007 | Fleenor |
| 7,169,146 B2 | 1/2007 | Truckai |
| 7,179,254 B2 | 2/2007 | Pendekanti |

(56) References Cited

U.S. PATENT DOCUMENTS

| | | |
|---|---|---|
| 7,195,627 B2 | 3/2007 | Amoah |
| 7,220,260 B2 | 5/2007 | Fleming |
| 7,238,195 B2 | 7/2007 | Viola |
| 7,250,048 B2 | 7/2007 | Francischelli |
| 7,267,677 B2 | 9/2007 | Johnson |
| 7,270,664 B2 | 9/2007 | Johnson |
| 7,276,068 B2 | 10/2007 | Johnson |
| 7,278,991 B2 | 10/2007 | Morris |
| 7,291,143 B2 | 11/2007 | Swanson |
| 7,364,577 B2 | 4/2008 | Wham |
| 7,367,972 B2 | 5/2008 | Francischelli |
| 7,410,483 B2 | 8/2008 | Danitz |
| 7,494,039 B2 | 2/2009 | Racenet |
| 7,506,790 B2 | 3/2009 | Shelton, IV |
| 7,540,872 B2 | 6/2009 | Schechter |
| 7,549,564 B2 | 6/2009 | Boudreaux |
| 7,624,902 B2 | 12/2009 | Marczyk |
| 7,641,651 B2 | 1/2010 | Nezhat |
| 7,703,653 B2 | 4/2010 | Shah |
| 7,794,461 B2 | 9/2010 | Eder |
| 7,803,156 B2 | 9/2010 | Eder |
| 7,862,565 B2 | 1/2011 | Eder |
| 7,942,874 B2 | 5/2011 | Eder |
| 2001/0001820 A1 | 5/2001 | Wampler |
| 2001/0029367 A1 | 10/2001 | Fleenor |
| 2002/0062123 A1 | 5/2002 | McClurken |
| 2002/0062136 A1 | 5/2002 | Hillstead |
| 2002/0107514 A1 | 8/2002 | Hooven |
| 2002/0111624 A1 | 8/2002 | Witt |
| 2002/0124853 A1 | 9/2002 | Burbank |
| 2002/0128643 A1 | 9/2002 | Simpson |
| 2002/0151882 A1 | 10/2002 | Marko |
| 2002/0177848 A1 | 11/2002 | Truckai |
| 2002/0183738 A1 | 12/2002 | Chee |
| 2003/0073994 A1 | 4/2003 | Schulze |
| 2003/0078577 A1 | 4/2003 | Truckai |
| 2003/0114851 A1 | 6/2003 | Truckai |
| 2003/0144652 A1 | 7/2003 | Baker |
| 2003/0144653 A1 | 7/2003 | Francischelli |
| 2003/0158547 A1 | 8/2003 | Phan |
| 2003/0171745 A1 | 9/2003 | Francischelli |
| 2003/0216726 A1 | 11/2003 | Eggers |
| 2003/0229344 A1 | 12/2003 | Dycus |
| 2003/0236549 A1 | 12/2003 | Bonadio |
| 2004/0006339 A1 | 1/2004 | Underwood |
| 2004/0010245 A1 | 1/2004 | Cerier |
| 2004/0068274 A1 | 4/2004 | Hooven |
| 2004/0097919 A1 | 5/2004 | Wellman |
| 2004/0122423 A1 | 6/2004 | Dycus |
| 2004/0143263 A1 | 7/2004 | Schechter |
| 2004/0199226 A1 | 10/2004 | Shadduck |
| 2004/0236320 A1 | 11/2004 | Protsenko |
| 2005/0010212 A1 | 1/2005 | McClurken |
| 2005/0015085 A1 | 1/2005 | McClurken |
| 2005/0021026 A1 | 1/2005 | Baily |
| 2005/0021027 A1 | 1/2005 | Shields |
| 2005/0033276 A1 | 2/2005 | Adachi |
| 2005/0033277 A1 | 2/2005 | Clague |
| 2005/0033278 A1 | 2/2005 | McClurken |
| 2005/0070895 A1 | 3/2005 | Ryan |
| 2005/0070978 A1 | 3/2005 | Bek |
| 2005/0090819 A1 | 4/2005 | Goble |
| 2005/0096645 A1 | 5/2005 | Wellman |
| 2005/0096694 A1 | 5/2005 | Lee |
| 2005/0107781 A1 | 5/2005 | Ostrovsky |
| 2005/0107784 A1 | 5/2005 | Moses |
| 2005/0113817 A1 | 5/2005 | Isaacson |
| 2005/0113820 A1 | 5/2005 | Goble |
| 2005/0119654 A1 | 6/2005 | Swanson |
| 2005/0124987 A1 | 6/2005 | Goble |
| 2005/0131390 A1 | 6/2005 | Heinrich |
| 2005/0149073 A1 | 7/2005 | Arani |
| 2005/0171533 A1 | 8/2005 | Latterell |
| 2005/0187561 A1 | 8/2005 | Lee-Sepsick |
| 2005/0192633 A1 | 9/2005 | Montpetit |
| 2005/0196421 A1 | 9/2005 | Hunter |
| 2005/0203500 A1 | 9/2005 | Saadat |
| 2005/0203504 A1 | 9/2005 | Wham |
| 2005/0209664 A1 | 9/2005 | Hunter |
| 2005/0226682 A1 | 10/2005 | Chersky |
| 2005/0256522 A1 | 11/2005 | Francischelli |
| 2005/0256524 A1 | 11/2005 | Long |
| 2005/0261676 A1 | 11/2005 | Hall |
| 2006/0025765 A1 | 2/2006 | Landman |
| 2006/0025812 A1 | 2/2006 | Shelton |
| 2006/0041254 A1 | 2/2006 | Francischelli |
| 2006/0047278 A1 | 3/2006 | Christian |
| 2006/0052778 A1 | 3/2006 | Chapman |
| 2006/0052779 A1 | 3/2006 | Hammill |
| 2006/0064084 A1 | 3/2006 | Haemmerich |
| 2006/0079872 A1 | 4/2006 | Eggleston |
| 2006/0079891 A1 | 4/2006 | Arts |
| 2006/0167451 A1 | 7/2006 | Cropper |
| 2006/0190029 A1 | 8/2006 | Wales |
| 2006/0199999 A1 | 9/2006 | Ikeda |
| 2006/0217709 A1 | 9/2006 | Couture et al. |
| 2006/0226196 A1 | 10/2006 | Hueil |
| 2006/0229665 A1 | 10/2006 | Wales |
| 2006/0253117 A1 | 11/2006 | Hovda |
| 2006/0258954 A1 | 11/2006 | Timberlake |
| 2006/0259035 A1 | 11/2006 | Nezhat |
| 2006/0271037 A1 | 11/2006 | Maroney |
| 2006/0271041 A1 | 11/2006 | Eder |
| 2006/0271042 A1 | 11/2006 | Latterell |
| 2006/0287674 A1 | 12/2006 | Ginn |
| 2006/0289602 A1 | 12/2006 | Wales |
| 2006/0293655 A1 | 12/2006 | Sartor |
| 2007/0005061 A1 | 1/2007 | Eder |
| 2007/0055231 A1 | 3/2007 | Dycus |
| 2007/0062017 A1 | 3/2007 | Dycus |
| 2007/0073340 A1 | 3/2007 | Shelton |
| 2007/0128174 A1 | 6/2007 | Kleinsek |
| 2007/0129726 A1 | 6/2007 | Eder |
| 2007/0173804 A1 | 7/2007 | Wham |
| 2007/0173805 A1 | 7/2007 | Weinberg |
| 2007/0173811 A1 | 7/2007 | Couture |
| 2007/0179497 A1 | 8/2007 | Eggers |
| 2007/0185482 A1 | 8/2007 | Eder |
| 2007/0208336 A1 | 9/2007 | Kim et al. |
| 2007/0244538 A1 | 10/2007 | Eder |
| 2007/0250113 A1 | 10/2007 | Hegeman |
| 2007/0265613 A1 | 11/2007 | Edelstein |
| 2007/0282318 A1 | 12/2007 | Spooner |
| 2007/0282320 A1 | 12/2007 | Buysse |
| 2008/0172052 A1 | 7/2008 | Eder |
| 2008/0188844 A1 | 8/2008 | McGreevy |
| 2008/0195093 A1 | 8/2008 | Couture |
| 2008/0221565 A1 | 9/2008 | Eder |
| 2008/0228179 A1 | 9/2008 | Eder |
| 2008/0275446 A1 | 11/2008 | Messerly |
| 2008/0308607 A1 | 12/2008 | Timm |
| 2009/0018535 A1 | 1/2009 | Schechter |
| 2009/0112246 A1 | 4/2009 | Weisshaupt |
| 2009/0138006 A1 | 5/2009 | Bales |
| 2009/0157071 A1 | 6/2009 | Wham |
| 2009/0157072 A1 | 6/2009 | Wham |
| 2009/0157075 A1 | 6/2009 | Wham |
| 2009/0182323 A1 | 7/2009 | Eder |
| 2009/0182333 A1 | 7/2009 | Eder |
| 2009/0198272 A1 | 8/2009 | Kerver |
| 2009/0209953 A1 | 8/2009 | Schoenman |
| 2009/0240245 A1 | 9/2009 | Deville |
| 2009/0299367 A1 | 12/2009 | Ginnebaugh |
| 2010/0042093 A9 | 2/2010 | Wham |
| 2010/0076427 A1 | 3/2010 | Heard |
| 2010/0094282 A1 | 4/2010 | Kabaya |
| 2010/0280508 A1 | 11/2010 | Eder |
| 2010/0298823 A1 | 11/2010 | Cao |
| 2011/0184404 A1 | 7/2011 | Walberg |
| 2011/0202058 A1 | 8/2011 | Eder |
| 2011/0230875 A1 | 9/2011 | Walberg |

(56) References Cited

U.S. PATENT DOCUMENTS

| | | | |
|---|---|---|---|
| 2011/0238056 | A1 | 9/2011 | Koss |
| 2012/0071871 | A1 | 3/2012 | Lue |

FOREIGN PATENT DOCUMENTS

| | | |
|---|---|---|
| CN | 1882289 | 12/2006 |
| CN | 1889893 | 1/2007 |
| DE | 202007005510 | 7/2007 |
| DE | 202007015547 | 2/2008 |
| DE | 102007017966 | 11/2008 |
| DE | 102007053359 | 6/2009 |
| DE | 202011000800 | 6/2011 |
| EP | 0134750 | 3/1985 |
| EP | 487269 | 5/1991 |
| EP | 440385 | 7/1991 |
| EP | 502268 | 9/1992 |
| EP | 562195 | 9/1993 |
| EP | 658333 | 6/1995 |
| EP | 0737446 | 10/1996 |
| EP | 875209 | 4/1998 |
| EP | 923907 | 6/1999 |
| EP | 1064886 | 1/2001 |
| EP | 833593 | 2/2001 |
| EP | 1254637 | 11/2002 |
| EP | 0717960 | 2/2003 |
| EP | 1293169 | 3/2003 |
| EP | 1293170 | 3/2003 |
| EP | 869742 | 5/2003 |
| EP | 873089 | 10/2003 |
| EP | 742696 | 11/2003 |
| EP | 1041933 | 3/2004 |
| EP | 1004277 | 7/2004 |
| EP | 959786 | 9/2004 |
| EP | 913126 | 10/2004 |
| EP | 956827 | 10/2004 |
| EP | 1472984 | 11/2004 |
| EP | 1486177 | 12/2004 |
| EP | 1518498 | 3/2005 |
| EP | 1518499 | 3/2005 |
| EP | 1532933 | 5/2005 |
| EP | 1621146 | 2/2006 |
| EP | 1632192 | 3/2006 |
| EP | 1645237 | 4/2006 |
| EP | 1747761 | 1/2007 |
| EP | 1767164 | 3/2007 |
| EP | 1810625 | 7/2007 |
| EP | 1852081 | 11/2007 |
| EP | 1862138 | 12/2007 |
| EP | 1039862 | 5/2008 |
| EP | 1707143 | 6/2008 |
| EP | 2106764 | 10/2009 |
| EP | 1330991 | 1/2011 |
| JP | 06337936 | 8/1994 |
| JP | 11137562 | 5/1999 |
| JP | 2001095813 | 4/2001 |
| JP | 2003088534 | 3/2003 |
| JP | 2004049566 | 2/2004 |
| JP | 2005144193 | 6/2005 |
| JP | 9005160889 | 6/2005 |
| WO | 9222257 | 12/1992 |
| WO | 9308754 | 5/1993 |
| WO | 9400060 | 1/1994 |
| WO | 9426179 | 11/1994 |
| WO | 9502371 | 1/1995 |
| WO | 9605776 | 2/1996 |
| WO | 1996016605 | 6/1996 |
| WO | 9623449 | 8/1996 |
| WO | 9724073 | 7/1997 |
| WO | 9724074 | 7/1997 |
| WO | 9812999 | 4/1998 |
| WO | 9843548 | 10/1998 |
| WO | 9853750 | 12/1998 |
| WO | 9923933 | 5/1999 |
| WO | 9952459 | 10/1999 |
| WO | 9956646 | 11/1999 |
| WO | 0013193 | 2/2000 |
| WO | 0013192 | 3/2000 |
| WO | 0112090 | 2/2001 |
| WO | 0135846 | 5/2001 |
| WO | 0154602 | 8/2001 |
| WO | 0158372 | 8/2001 |
| WO | 0158373 | 8/2001 |
| WO | 0182812 | 11/2001 |
| WO | 0224092 | 3/2002 |
| WO | 0267798 | 7/2002 |
| WO | 0258542 | 8/2002 |
| WO | 03088806 | 10/2003 |
| WO | 03103522 | 12/2003 |
| WO | 2004032596 | 4/2004 |
| WO | 2004032776 | 4/2004 |
| WO | 20040734090 | 9/2004 |
| WO | 2004098383 | 11/2004 |
| WO | 2005009213 | 2/2005 |
| WO | 2005034729 | 4/2005 |
| WO | 2005079901 | 9/2005 |
| WO | 05115251 | 12/2005 |
| WO | 2006060431 | 6/2006 |
| WO | 2006124601 | 11/2006 |
| WO | 2007002227 | 1/2007 |
| WO | 2007082061 | 7/2007 |
| WO | 2008094554 | 8/2008 |
| WO | 2008124112 | 10/2008 |

OTHER PUBLICATIONS

Office Action for U.S. Appl. No. 13/536,149 dated Oct. 6, 2014.
Aoki et al.; Thoracoscopic resection of the lung with the ultrasonic scalpel.; Ann Thorac Surg; vol. 67; No. 4; pp. 1181-1183; Apr. 1999.
Arthrocare receives clearance to market coblation-based devices for gynecology and laparoscopic surgery: clearance includes plasma forceps and 21 specific indications; Business Wire; p. 524; Oct. 25, 2001.
Australian Examination Report issued in Australian Application No. 2011212786, dated Apr. 16, 2014.
Bergamaschi et al.; Laparoscopic intracorporeal bowel resection with ultrasound versus electrosurgical dissection; JSLS; vol. 5; No. 1; pp. 17-20; Jan.-Mar. 2001.
Chinese Examination Report for Application No. 200780053005.9 dated Oct. 18, 2011 with English Language Translation.
Chinese Office Action dated Mar. 19, 2012, for related Chinese Application No. 200880005613.7 (w/English translation) 15 pgs.
Chinese Application No. 200780053005.9, fourth office action dated Mar. 27, 2013.
Curon Announces the Publication of Data Supporting Durability and Effectiveness of Stretta (R) System: —Positive One Year Follow-Up Data of U.S. Clinical Trial Published in Gastrointestinal Endoscopy: Feb. 7, 2002; PR Newswire, pNYTH 10307022002.
Curon Medical Announces Presentation of Positive Clinical Study Results of Stretta(R) Procedure For Gastroesophageal Reflux Disease (GERD): Mar. 20, 2002; PR Newswire,PNYW07920032002.
Eder, Joseph C.; U.S. Appl. No. 12/200,798 "Assisted systems and methods for performing transvaginal hysterectomies," filed Aug. 28, 2008.
Eichfeld et al.; Evaluation of ultracision in lung metastatic surgery; Ann Thorac Surg; vol. 70; No. 4; pp. 1181-1184; Oct. 2000.
Enable Medical Introduces Second Generation Bipolar Scissors: Dec. 1998: Health Industry Today, pNA.
Entire patent prosecution history of U.S. Appl. No. 13/021,633, filed Feb. 4, 2011, entitled, "Laparoscopic Radiofrequency Surgical Device."
ERBE Elektromedizin GmbH ERBE BiClamp Brochure; downloaded Jan. 24, 2011; 6 pgs., © 2011, http://vvvvw.erbe-med.corn/erbe/media/Marketingmaterialen/85100-139_ERBE_EN_BiClamp_D024676.pdf.
European Patent Office Examination Report for European Application No. 07 811 938.5 dated Mar. 5, 2012.
Everest Medical Announces Introduction of 3mm Bipolar Forceps: Oct. 2, 1996: PRNewswire, p. 1002MNW021.

(56) References Cited

OTHER PUBLICATIONS

Everest Medical Discusses Patent Status: Forecasts $1 Million Revenue First Quarter: Introduces Next Generation Bipolar Scissors: Mar. 31, 1994; PR Newswire, p. N/A.
Everest Medical Introduces New Quadripolar (TM) Cutting Forcepts at The Global Congress of Gynecologic Endoscopy Meeting: Nov. 8, 1999; PR Newswire p. 8927.
Everest Medical Reports Record First Quarter Results: Introduces Next Generation Bipolar Scissors: Apr. 19, 1994; PR Newswire, p. N/A.
Examination Report for Australian Patent Application No. 200. 7352602 dated Aug. 21, 2012.
Examination Report for Chinese Patent Application No. 200780053005.9: dated Jun. 26, 2012 (w/ English Language Translation).
First Office Action in Related Chinese Application No. 201180003207.9 dated Jul. 9, 2014.
Gyrus ACMI (an Olympus Company); PKS Seal (product page);http://www.gyrusacmi.com/user/display.cfm?display=product&pid=9024; downloaded Jan. 24, 2011; 1 page.
Gyrus Medical: Cutting Forceps Forceps:http://www.gyrusgroup.com/medical/products_item.asp?id=7, downloaded 2005.
Gyrus Medical: LP Scissors:http://www.gyrusgroup.com/medical/products item.asp?id=11, downloaded 2005.
Gyrus Medical; Lyons TM Dissecting Forceps: http://www.gyrusgroup.com/medical/products item.asp?id=8, downloaded 2005.
Gyrus Medical; Micro/Macro-Jaw Forceps: http://www.gyrusgroup.com/medical/products item.asp?id=13, downloaded 2005.
Gyrus Medical; Seal Open Forceps (Product Information); downloaded Oct. 20, 2005.
Hayashi et al.; Experimental and clinical evaluation of the harmonic scalpel in thoracic surgery; Kurume Med J; vol. 46; No. 1; pp. 25-29; 1999.
Hefni et al.; Safety and efficacy of using the ligasure vessel sealing system for securing the pedicles in vaginal hysterectomy: randomized controlled trial; BJOG vol. 112; No. 3; pp. 329-333; Mar. 2005.
Heniford ST et al.: Initial Results With an Electrothermal Bipolar Vessel Sealer: Aug. 2001 Surg Endosc.; 15 (8); 799-801, Epub May 14, 2001; Carolinas Laparoscopic and Advanced Surgery Prograrn, Department of General Surgery, Carolinas Medical Center, 1000 Blythe Boulevard, MEB #601, Charlotte, NC. USA.
International Search Report for International Application No. PCT/US2011/023731, dated Oct. 13, 2011.
Japanese Examination Report for Application No. 2010-506177, dated Sep. 29, 2011 with English Language Translation.
Kamat. AA et al: Superiority of Electrocautery Over the Suture Method for Achieving Cervical Cone Bed Hemostasis: Oct. 2003. Obstet Gynecol.: 102 (4): 726-30; Department of Obstetrics and Gynecology, Baylor College of Medicine, Houston, Texas 77030, USA. akamat©bcm.tmc.edu.
Kennedy. JS et al.: High-Burst-Strength. Feedback-Controlled Bipolar Vessel Sealing; Jun. 1998 Surg Endosc.; 12 (6): 876-8; Valleylab, Inc., 5920 Longbow Drive, Boulder, CO 80301, USA.
Kerver et al., U.S. Appl. No. 13/070,391 entitled "Articulable electrosurgical instrument with a stabilizable articulation actuator," filed Mar. 23, 2011.
Kim et al.; Design and fabrication of a locomotive mechanism for capsule-type endoscopes using shape memory alloys (SFAs); IEEE/ASME Trans on Mechatronics; vol. 10; No. 1; pp. 77-86; Feb. 2005.
Koss et al.; U.S. Appl. No. 12/748,229 entitled "Irnpedance mediated power delivery for electrosurgery," filed Mar. 26, 2010.
Koss et al.; U.S. Appl. No. 12/907,646 entitled "Impedance mediated control of power delivery for electrosurgery," filed Oct. 19, 2010.
Kovac, Transvaginal hysterectomy; rationale and surgical approach; Obstet. Gynecol.; vol. 103; pp. 1321-1325; 2004.
Landman J. et al.: Evaluation of a Vessel Sealing System. Bipolar Electrosurgery. Harmonic Scalpel. Titanium Clips. Endoscopic Gastrointestinal Anastomosis Vascular Staples and Sutures For Arter lai and Venous Ligation in a Porcine Model: Feb. 2003. J Urol.; 169 (2): 697-700; Department of Surgery (Division of Urology), Washington University School of Medicine, St. Louis, Missouri, USA.
Levy. Barbara: Use of a New Vessel Ligation Device During Vaginal Hysterectomy: As presented at FIGO 2000, Washington, D.C; University of Washington School of Medicine; Federal Way, Washington, USA; © 2000 Valleylab.
Levy. Barbara et al.: Update on Hysterectomy: New Technologies and Techniques; Feb. 2003; http://www.obgmanagement.com/supplements.pdf/hysterectomy.pdf; A supplement to OBG Management.
Lin et al.; Application of ultrasonic scalpel in gynecologic operative laparoscopy; Chin Med J (Engl.); vol. 114; No. 12; pp. 1283-1285; Dec. 2001.
Live Tissue Connect Technologies; company profile;(http://www.onemedplace.com/database/compdisplay print.php?CompanyID=11508); 1 pg.; Oct. 19, 2010 (downloaded Feb. 7, 2011).
Lyons et al.; An innovative bipolar instrument for laparoscopic surgery; JSLS; vol. 9; No. 1; pp. 39-41; Jan.-Mar. 2005.
McClurken et al.; Collagen shrinkage and vessel sealing; Technical brief #300. Dover, NH: Tissue Link Medical; 2001.
Nezhat etal.; U.S. Appl. No. 08/948,282 entitled "Method and systems for organ resection," filed Oct. 9, 1997.
Nojarov et al.; High-energy scissors mode; Rhys Rev C Nucl Rhys; vol. 51; No. 5; pp. 2449-2456; 1995 (http://arxiv.org/abs/nucl-th/9502001v1).
Parikh et al.; Three dimensional virtual reality model of the normal female pelvic floor; Annals of Bimedical Engineering; vol. 32; pp. 292-296.
Preliminary Report on Patentability for Application No. PCT/US2011/023731 dated Aug. 7, 2012.
Quadripolar Cutting Forceps Introduced by Everest Medical: Jan. 2000; Health Industry Today, v. 63, n. 1. p. NA.
Radiofrequency energy proven effective against leading cause of obstructive sleep apnea; Business Wire: , Sep. 14, 1998, 4 pgs.
Refractec, Inc.; Medical Use of Radiofrequency (RF) Energy; (http://www.locateadoc.com/Site_tools/Print.cfm); 2 pgs; Aug. 23, 2008.
Sages 2001 Hands-On Course I—Taking it to the Next Level: Advanced Laparoscopic Techniques; http://www.sages.org/01/program/syllabi/ho1.html#schirme; 24 pgs; downloaded Oct. 5, 2005.
SAGES 2001 Nurses Program, Session 1,http://sages.org/01program/syllabi/nurse/nurse.html; downloaded Jan. 24, 2011; 5 pgs.
Srisombut. C. et al.: Laparoscopic Hysterectomy Using Laparosonic Coagulating Shears: Experience of 15 Cases: Aug. 2000. J. Med. Assoc. Thai.; 83 (8):915-20; Department of Obstetrics and Gynecology, Faculty of Medicine, Ramathibodi Hospital, Mahidol University, Bangkok, Thailand.
SURGRX 510(K) Summary (# K031133); Palo Alto, CA; 5 pgs.; Jul. 3, 2003.
The Gynecare Versapoint,.All contents copyright ® Johnson & Johnson Gateway, LLC, downloaded 2005, http://www.jnjgataway.com/home.jhtml?loc=USENG&page=viewContent&contentId=edeaO00100001747&parentId=fc0de00100000334.
TREAT; A new thermal device for sealing and dividing blood vessels; http://www.starioninstruments.com/PDFs/Treat.pdf; downloaded Jun. 29, 2005; 2 pgs.
Tyco Healthcare; The LigaSureVessel Sealing System (Brochure); Apr. 2002; 8 pgs.
U.S. Patent Issued For Novare Surgical Systems Cygnet (R) Surgical Clamp; Novare Signs Multi-Year Supply Agreement with Boston Scientific; PR Newswire, pNA; Sep. 2, 2003.
Valleylab Products—Electrosurgical Forceps: The Surgeon's Choice For Quality and Precision: htto://www.valleylab.com/oroduct/es/accessories/forceps over.html: © 2005 valleylab.
Valleylab Products—Ligasure TM Vessel Sealing System; http://www.valleylab.com/products/vessel__seal/index.html, © 2005.

(56) References Cited

OTHER PUBLICATIONS

Office Action dated Aug. 19, 2015 in U.S. Appl. No. 13/021,633.
Non-Final Office Action dated Nov. 6, 2015 in U.S. Appl. No. 13/536,149.
Notice of Allowance for U.S. Appl. No. 13/536,149, dated Jan. 13, 2016.
Non-Final Office Action dated Mar. 31, 2016 for U.S. Appl. No. 13/021,633.
Final Office Action for U.S. Appl. No. 13/021,633, dated Sep. 13, 2016, 17 pages.
U.S. Non-Final Office Action for U.S. Appl. No. 13/021,633, dated May 10, 2017, 19 pages.
Notice of Allowance for U.S. Appl. No. 13/021,633, dated Nov. 3, 2017, 12 pages.

ELECTROSURGICAL TISSUE DISSECTING DEVICE

CROSS-REFERENCE TO RELATED APPLICATIONS

This application is a continuation under 35 U.S.C. § 120 of U.S. patent application Ser. No. 13/536,149, filed Jun. 28, 2012, which in turn, claims the benefit of priority under 35 U.S.C. § 119 of U.S. Provisional Patent Application No. 61/502,268, filed Jun. 28, 2011, the contents of both applications being incorporated by reference herein in their entirety for any and all purposes.

FIELD

The disclosed technology relates to systems and methods for electrosurgery. More particularly, the technology relates to devices, methods, and systems of electrosurgical tissue dissection and tissue sealing.

BACKGROUND

The technology provided in this disclosure relates to electrosurgical devices, methods, and systems for electrosurgical procedures as enabled by bipolar radiofrequency energy.

SUMMARY

The technology provided in this disclosure relates to electrosurgical devices, methods, and systems for electrosurgical procedures as enabled by bipolar radiofrequency energy. Some technology embodiments are dedicated to electrosurgical dissection, other embodiments include a combination of electrosurgical dissection and tissue sealing capabilities. A dual modality device advantageously allows a minimization of device laparoscopic entry-exit events during a surgical procedure that involves (or may involve) both electrosurgical dissection and sealing.

BRIEF DESCRIPTION OF THE DRAWING FIGURES

DETAILED DESCRIPTION

Examples of embodiments of the technology are provided hereinafter. Particular technology features are described in the context of these various embodiments. Technology features that may be described or depicted in any one particular embodiment may also be applied to any other embodiment.

Figure 1:
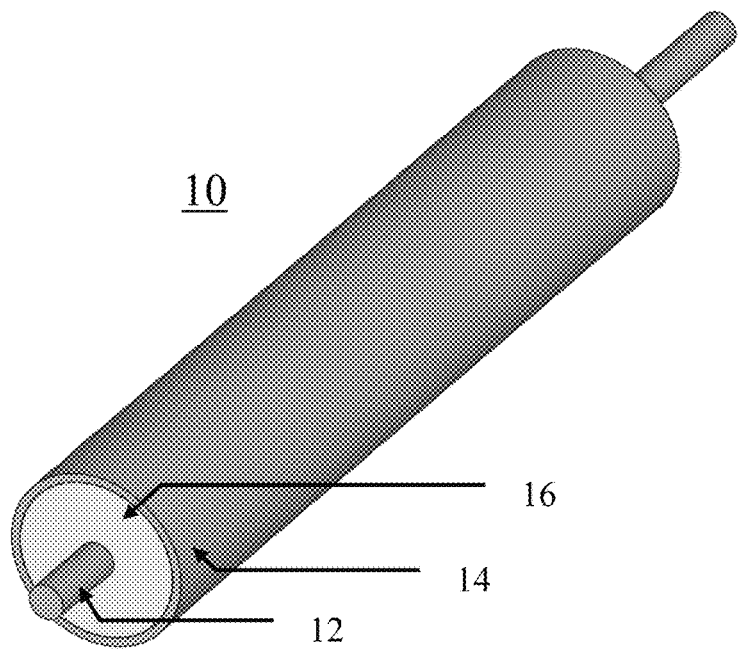
FIG. 1 depicts a tissue dissector including a concentric bipolar electrode pair, according to one exemplary embodiment of the invention.
Figure 2:
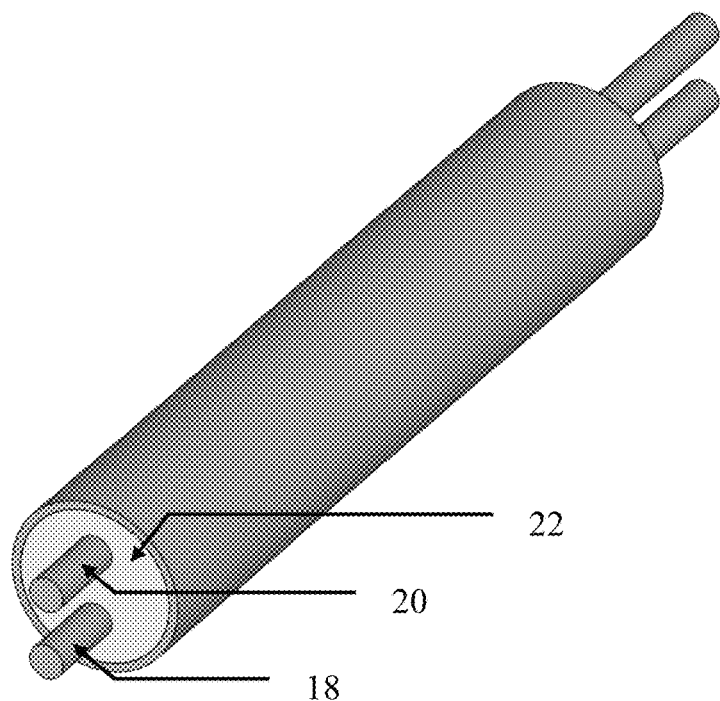
FIG. 2 depicts a tissue dissector including two side-by-side bipolar electrodes, according to another exemplary embodiment of the invention.

FIGS. 1 and 2 depict a first group of embodiments of the technology including a tissue dissector which takes the form of a point-focused dissector. The device of FIG. 1 includes an electrode assembly 10 that includes a distally directed pair of bipolar electrodes including a first electrode 12 and a second electrode 14, the electrodes disposed in a concentric configuration; and an isolating layer 16 disposed between the first and second electrodes.

In the alternative configuration shown in FIG. 2, the electrodes 18 and 20 are disposed in a side-by-side configuration with an isolating layer 22 separating the electrodes from each other. This first group of devices shown in FIGS. 1 and 2 is typically used for kinetically dissecting along a desired line of dissection, or for point-focused dissection.

Figure 3:
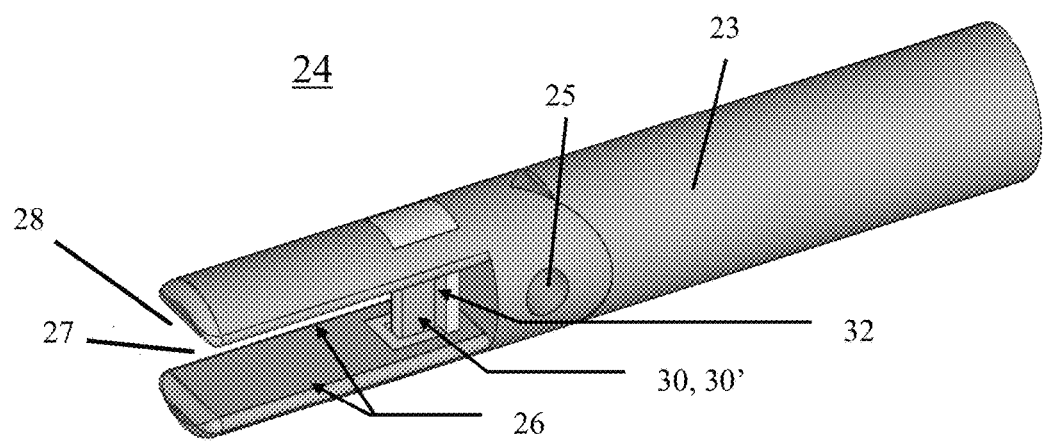
FIG. 3 depicts a tissue dissector including two forked tines and an internal blade, all in a fixed position, according to yet another exemplary embodiment of the invention.
Figure 4:
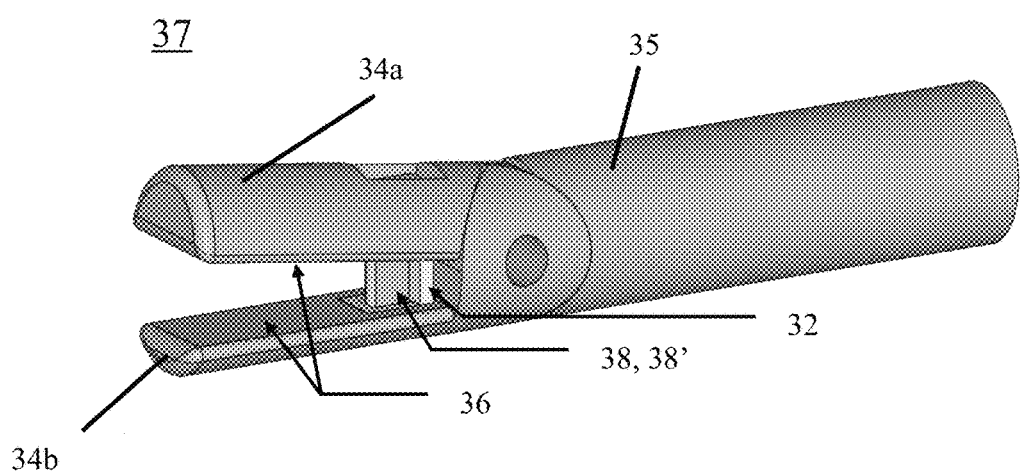
FIG. 4 depicts a tissue dissector including two forked tines, at least one of which is pivotable, and an internal blade, according to yet another exemplary embodiment of the invention.
Figure 5:
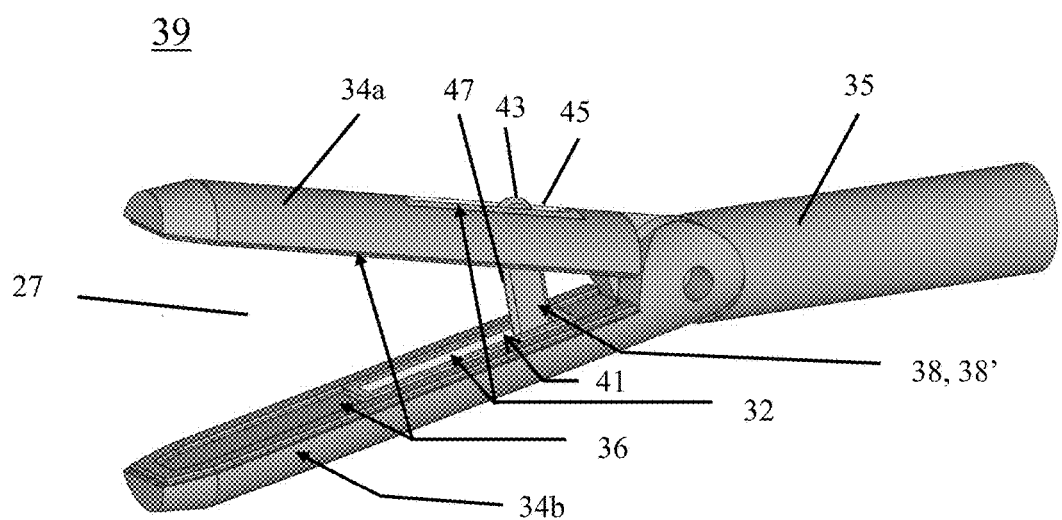
FIG. 5 depicts a tissue dissector including two jaws, at least one of which is pivotable, and an internal blade that pivots upward from the second jaw (but which cannot flip to an external position), according to another exemplary embodiment of the invention.

A second group of embodiments of the technology shown in FIGS. 3-5, takes the form of a device with a tissue-receiving window for distally advancing kinetic dissection. In this application, "kinetic dissection" generally refers to a dissection that is driven by manual movement of the electrode assembly, or the device as a whole, by an operator such as a surgeon. Embodiments may vary with regard to whether the tines are fixed or pivotable, as will be described hereinafter.

More particularly, FIG. 3 depicts an electrode assembly 24 that includes a shaft 23, a pair of directed tines 26 that are distal to the shaft 23. The tines 26 are in a substantially parallel forked configuration, the forked configuration comprising a gap 27 between the tines 26. The tines 26 and the gap 27 collectively comprise a distal-facing tissue receiving window 28.

The electrode assembly 24 includes a pair of bipolar electrodes, including a first electrode and a second electrode.

More particularly, the first and second tines 26 act collectively as a first bipolar electrode 26'. The second electrode 30 is in the form of an electrosurgical blade 30' and is disposed orthogonally across a proximal aspect of the gap 27 between the tines 26. An isolator layer 32 electrically separates the first and second electrodes 26' and 30.

Tissue that comes into contact with either or both of the tines 26 and the electrosurgical blade 30' at the same time is subject to dissection by electrosurgical energy delivered by the device. The tines 26 are fixed such that they are not pivotable with respect to each other, however, the tines 26 are pivotable with respect to the shaft 23 about a pivot point 25. Alternatively, the tines 26 may be fixed to the shaft 23 such that the tines 26 can not pivot with respect to the shaft 23.

FIGS. 4 and 5 depict dedicated tissue dissector devices 37 and 39, respectively, that are each configured as an electrode assembly including a set of opposable jaws 34a and 34b (referred to collectively as jaws 34) that can move between an open and a closed position. Accordingly, an electrode assembly of this type of device includes a set of opposing jaws 34. The jaws 34 are moveable from a closed position to an open position (see FIG. 4, for example). When the jaws 34 are in an open position, the electrodes 36 and 38 form a distal-facing tissue trap that is configured and arranged to dissect a tissue sheet kinetically, as when the electrode assembly is distally advanced by an operator. In another aspect, the opposing jaws 34 may also be configured to be able to dissect from a fixed position, as when the jaws 34 close around a tissue site.

In FIG. 4 the opposable jaws 34 are configured such that jaw 34b is fixed with respect to the shaft 35 to which it is attached, and the other jaw 34a is pivotable with respect to the shaft 35. In FIG. 5, both jaws 34 are pivotable with respect to the shaft 35.

Bipolar electrodes 36 and 38 are arranged in FIGS. 4 and 5 of the electrode assembly in a manner similar to that as described for FIG. 3. Tissue that comes into contact with either or both of the jaws 34 and the electrosurgical blade 38' at the same time is subject to dissection by electrosurgical energy delivered by the device 37 and 39.

In the second group of embodiments of the technology shown in FIGS. 3-5, at least one of the jaws (or tines) or the electrosurgical blade may comprise a plurality of electrodes 36 and 38, the electrode assembly thereby comprising a plurality of bipolar electrode pairs 36 and 38. The devices further include an isolator 32 or electrically insulative layer that electrically isolates the first and second electrodes 36 and 38 from each other.

In various embodiments of the opposable jaws of FIGS. 4 and 5, the jaws 34a and 34b are capable of being open at an angle of up to about 90 degrees. The jaws 34a and 34b may be further configured to lock or stabilize in an open position at a desired angle.

FIG. 5 depicts an electrosurgical blade element 38' that is movable between at least two different positions. The movable blade 38' is pivotably attached to the lower jaw 34b in this exemplary embodiment by a pin (not shown) located at the lower, proximal end of the blade 38'. In a first position (not shown), the blade 38' is pivoted distally and downwardly until it is retracted within a slot 41 located in the lower jaw 34b. In the second position shown in FIG. 5, the blade 38' is pivoted upwardly and proximally such that it spans between the upper and lower jaws 34, with the distal tip 43 of the blade 38' received within a slot 45 of the upper jaw 34bIn all positions, the blade 38' is electrically isolated from both the upper and lower jaws 34 in this embodiment.

Although not shown, a suitable mechanism and/or electronic, pneumatic or hydraulic circuit may be employed to operationally connect the blade 38' to a blade actuator (not shown) located near the proximal end (i.e., toward shaft 35) of the device 39 or external to the device 39.

When the electrosurgical blade 38' of FIG. 5 is in the deployed second position as described above, RF energy may be passed between the blade 38' and the first electrode 36, which, in this example, is both the upper and lower jaws 34. The RF energy delivered through the blade 38' to the tissue is sufficient to electrosurgically cut the tissue as the blade 38' moves through the tissue. The edges of the blade 38' including the leading distal edge 47 may be configured as blunt edges such that all cutting is performed electrosurgically. Alternatively, the leading distal edge 47 of the blade 38' may be sharpened so that cutting may occur manually simply by forward movement of the instrument, with or without additional electrosurgical cutting. Depending on the application, the cutting or dissection, performed with or without the use of RF energy, may involve pure cutting with no concurrent hemostasis, may involve some coagulation, or may involve coagulation with complete hemostasis.

Figure 10A:
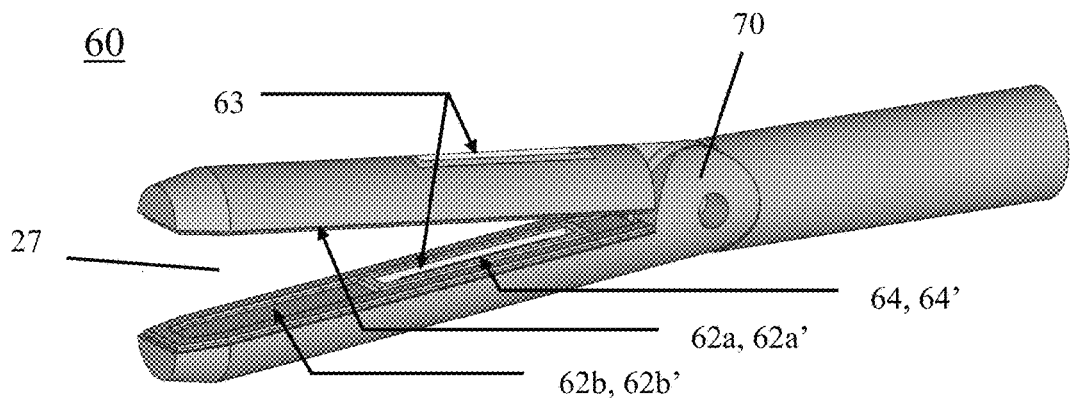
FIG. 10A depicts a tissue dissector and sealer including a pivotable blade shown in a neutral position, according to yet another exemplary embodiment of the invention.
Figure 10B:
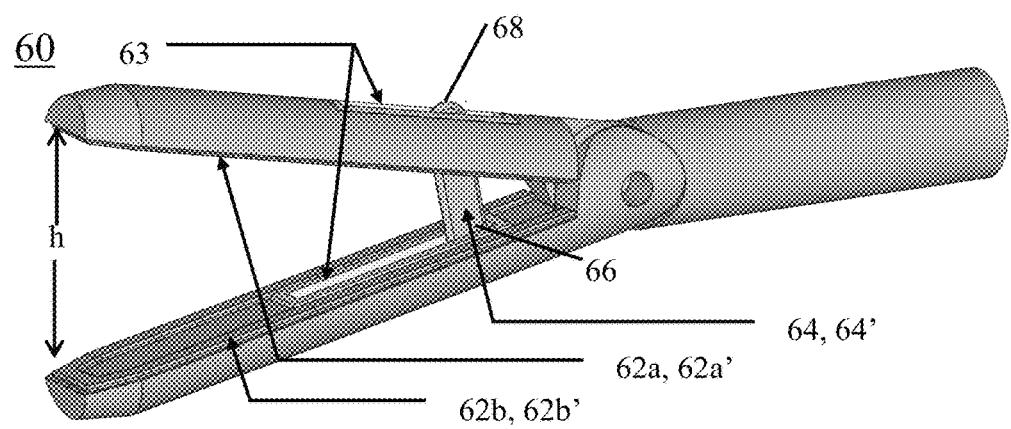
FIG. 10B depicts the tissue dissector and sealer of FIG. 10A with the blade shown between the jaws.
Figure 10C:
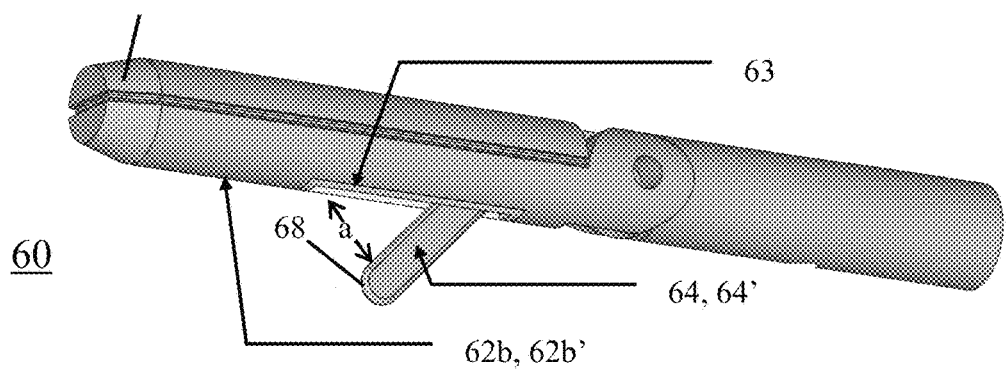
FIG. 10C depicts the tissue dissector and sealer of FIG. 10A with the blade shown external to the jaws.

The device 39 shown in FIG. 5 resembles embodiments of a fourth group, as described further below with reference to FIGS. 10A-10C. For example, the immediately preceding description regarding the deployment of an electrosurgical blade 38' in the context of FIG. 5 also substantially applies to FIGS. 10A-10C. However, the device 39 shown in FIG. 5, in contrast to the device 60 shown in FIGS. 10A-10C, is a dedicated dissecting instrument, without tissue sealing capability. Further, while the electrosurgical blade 38' of FIG. 5 is configured to be able to move into the gap 27 between the jaws 34; the electrosurgical blade 38' is not free to pivot to a position external to the jaws 34.

Additionally, the construction of the electrode assembly of FIG. 5, which comprises electrodes 36 and 38, can be relatively light in comparison to the device 60 of FIGS. 10A-10C. More particularly, the device 39 of FIG. 5 is not required to effect compression forces associated with tissue sealing. Finally, it should be understood that the electrosurgical blade 38' of FIG. 5 may be able to rotate externally outward beyond the jaws 34, thereby forming a device configuration that is particularly similar to that of the device 60 of FIGS. 10A-10C.

A third group of embodiments of the technology shown in FIGS. 6A-9B, takes the form of a dedicated dissector device 51a-51d (referred to collectively as device 51) that includes a handle or shaft 49, a distally directed member 57 and an electrosurgical blade 55a-55d (referred to collectively as blade 55) that is moveably coupled with respect to the shaft 49 and the distally directed member 57. The distally directed member 57 is the first electrode 57' of the device 51, and the electrosurgical blade 55 is the second electrode 55' of the device 51. Some of these embodiments may be operated with a manually driven movement of the device 51, and consequently, movement of the electrode assembly along a targeted line of dissection. This type of movement driven dissection is referred to as kinetic dissection.

The third group of embodiments shown in FIGS. 6A-9B are dedicated dissecting devices, with electrosurgical blades that are pivotable or otherwise movable such that at least a portion of the blade 55 is exposed into a position that can engage tissue for dissection. The projecting blade 55 of this and other embodiments of the present disclosure provides the ability to cut through layers of tissue to gain access to target tissue. For example, the projecting blade allows cutting through adhesions to gain access to an organ, or cutting around a tissue mass, which may be difficult or impossible using a cutting blade located between two jaw members. In some embodiments, the distance that the blade 55 projects from the device is adjustable. This allows for controlled depth cutting of tissue and/or vessel sealing.

One embodiment of this third embodiment shown in FIGS. 6A-9B has an electrode assembly that includes a distally directed member 57 comprising a first electrode 57' of a bipolar electrode pair, and an electrosurgical blade 55 comprising a second electrode 55a'-55d' (referred to collectively as second electrode 55') of the bipolar electrode pair.

Embodiments of the blade 55 are configured to be moveable from a home position (see FIGS. 6A, 7A, 8A and 9A), wherein the blade 55 is longitudinally aligned with the distally directed member 57, to any of a range of outwardly projected positions (see FIGS. 6B, 7B, 8B and 9B), wherein the blade 55 projects beyond the longitudinal profile of the distally directed member 57. An isolator 59 or electrically insulative layer typically isolates the first and second electrodes 57' and 55' from each other from electrical contact.

In some of the devices of the third embodiment shown in FIGS. 6A-9B, at least one of the distally directed member 57 and the electrosurgical blade 55 comprises a plurality of electrodes 57' and 55', the electrode assembly thereby comprising a plurality of bipolar electrode pairs.

The electrode assemblies of FIGS. 6A-9B are configured to effect a controlled-depth tissue cut when the electrode housing assembly is moved across a target tissue surface by an operator. Such operator-driven movement may include any of distally directed translational movement, proximally directed translational movement, or lateral movement. Movements of this type across or through tissue, to a certain depth, may be useful in various surgical maneuvers. For example, this type of dissection may be directed to an exposing function, to access to an underlying site of interest. Or, it may be directed to an exfoliating function, where a portion of a layer of tissue is being removed.

In some of the devices 51 of FIGS. 6A-9B, the electrosurgical blade 55 may be pivotably connected to the distally directed member 57, such pivotable connection allowing the blade 55 to attain a position wherein at least a portion of the blade 55 projects beyond the longitudinal profile of the distally directed member 57. In various embodiments of FIGS. 6A-9B, the site of a pivotable connection of the blade 55 to the distally directed member 57 may be disposed at any appropriate position along the blade 55 between its proximal end 61 and distal end 63. In various embodiments of FIGS. 6A-9B, the electrosurgical blade 55 is pivotably connected to the distally directed member 57 such that it has a pivotable arc range of up to 90 degrees from the site of its connection.

A variety of other mechanisms may allow the electrosurgical blade 55 to be projected beyond the longitudinal profile of the distally directed member 57. For example, in some embodiments of FIGS. 6A-9B the electrosurgical blade 55 may be projectable beyond the longitudinal profile of the distally directed member 57 by a foldable mechanism.

With regard to being configured to be able to cut to a controlled depth, when the electrosurgical blade 55 is positioned in an outwardly projected position (see FIGS. 6B, 7B, 8B and 9B), a distance 'd' between a point that projects most further from the longitudinal profile of the distally directed member 57 defines a cutting zone depth. In some embodiments, the electrosurgical blade 55 is lockable or stabilizable at any position within an arc of its pivotable range.

Figure 6A:
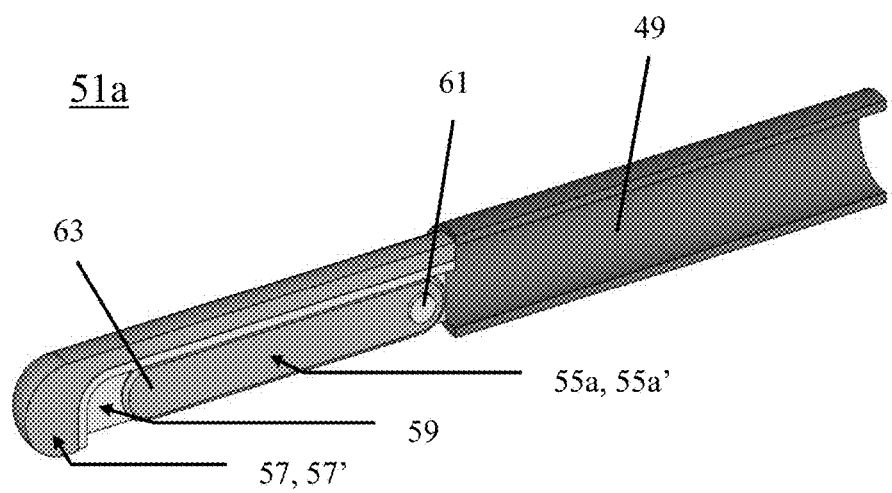
FIG. 6A depicts a tissue dissector including a blade having a proximal pivot point, as shown in a closed position, according to another exemplary embodiment of the invention.
Figure 6B:
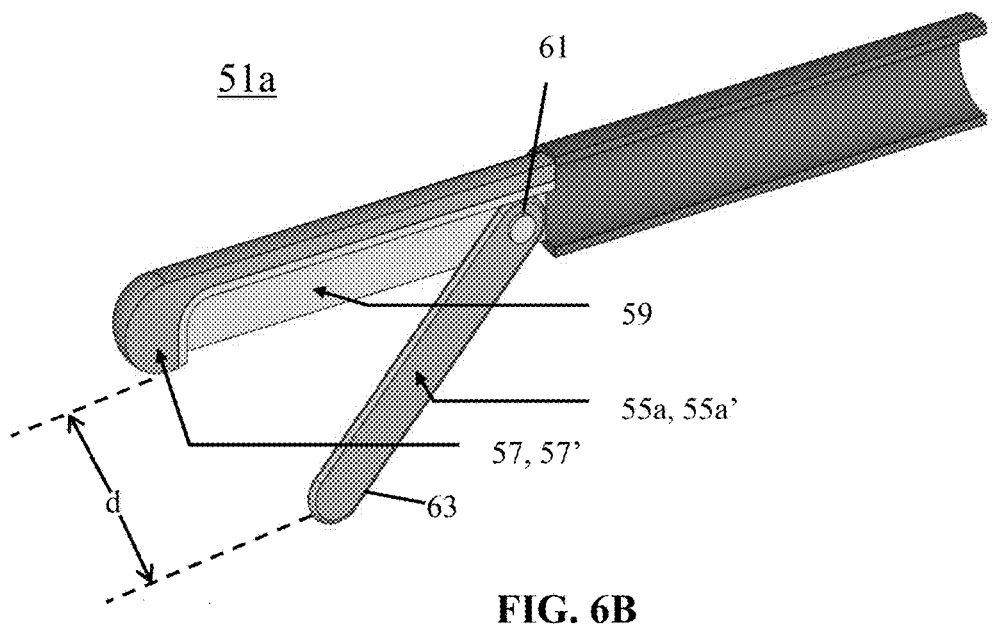
FIG. 6B depicts the tissue dissector of FIG. 6A with the blade shown in an open position.

In the device of FIGS. 6A and 6B, the blade 55a is pivotably connected to the isolator 59 at a proximal location on the isolator 59 (i.e., at a location toward the shaft 49 and away from the free end of the distally directed member 57). The isolator 59 is defined on an elongated recess that is formed on a surface of the distally directed member 57.

Figure 7A:
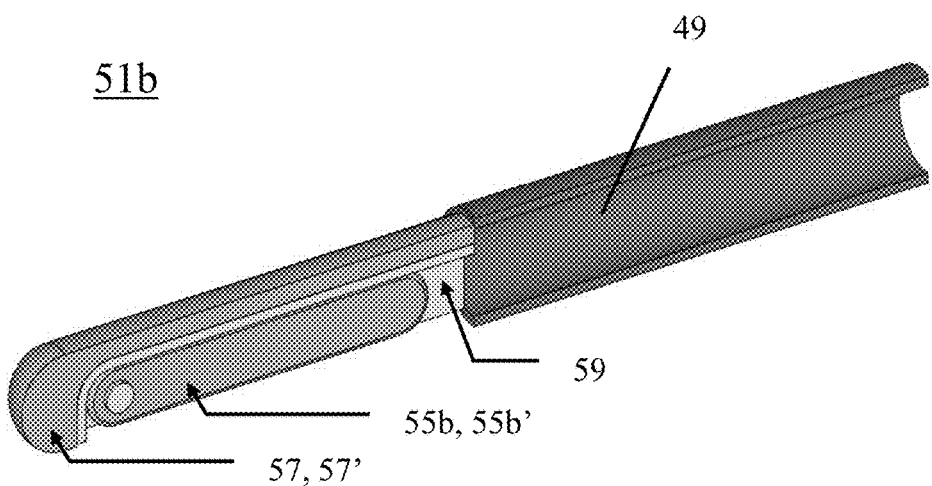
FIG. 7A depicts a tissue dissector including a blade having a distal pivot point, as shown in a closed position, according to another exemplary embodiment of the invention.
Figure 7B:
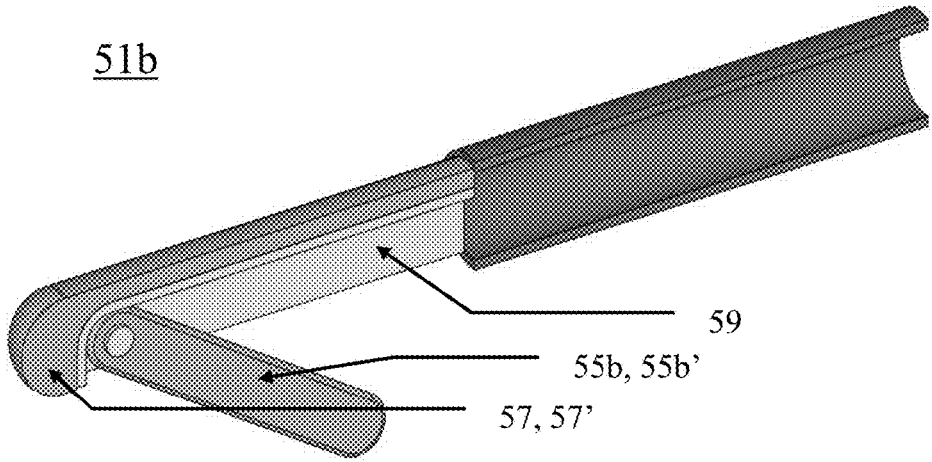
FIG. 7B depicts the tissue dissector of FIG. 7A with the blade shown in an open position.

In the device of FIGS. 7A and 7B, the blade 55b is pivotably connected to the isolator 59 at a distal location on the isolator 59 (i.e., at a location away from the shaft 49 and toward the free end of the distally directed member 57).

Figure 8A:
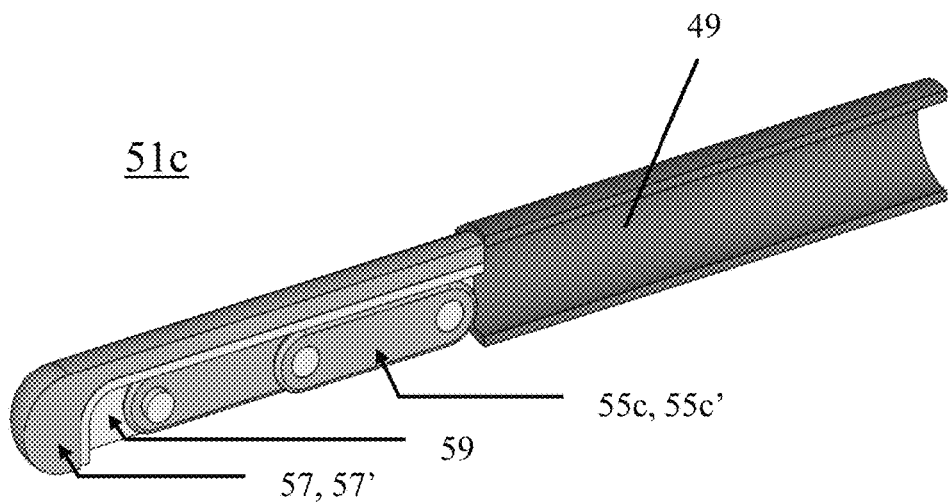
FIG. 8A depicts a tissue dissector including a blade having a foldable projecting mechanism, as shown in a closed position, according to yet another exemplary embodiment of the invention.
Figure 8B:
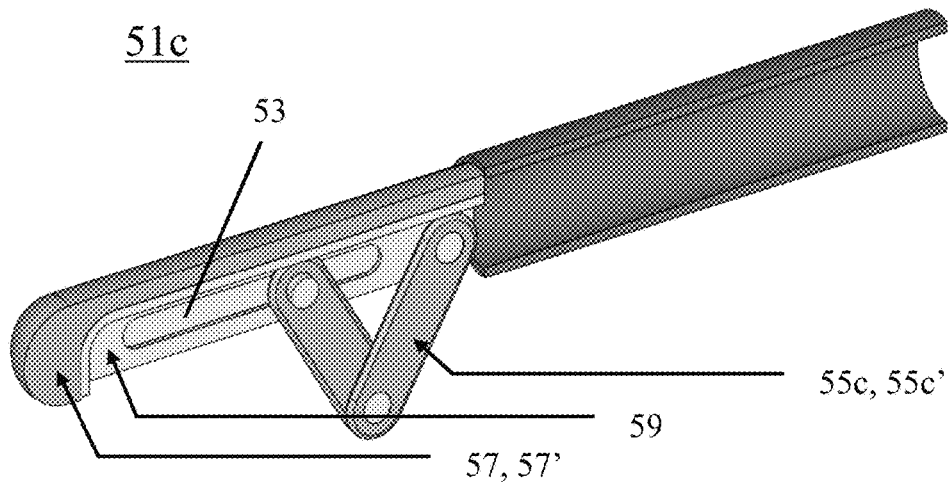
FIG. 8B depicts the tissue dissector of FIG. 8A with the blade shown in an open position.

In the device of FIGS. 8A and 8B, the blade 55c comprises a linkage having two links that are pivotably connected together by a pin. One link of the linkage is pivotably connected to the isolator 59 at a proximal location on the isolator 59, and the other link of the linkage is slidably connected to an elongated slot 53 that is defined in the isolator 59. The links of the linkage are configured to pivot with respect to one another, as depicted in FIG. 8B.

Figure 9A:
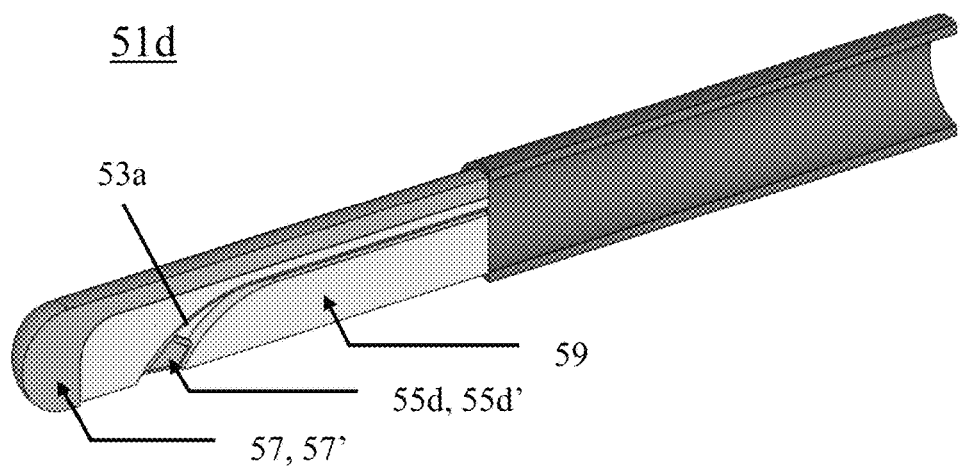
FIG. 9A depicts a tissue dissector including a blade having a flexible projecting mechanism, as shown in a home position, according to yet another exemplary embodiment of the invention.
Figure 9B:
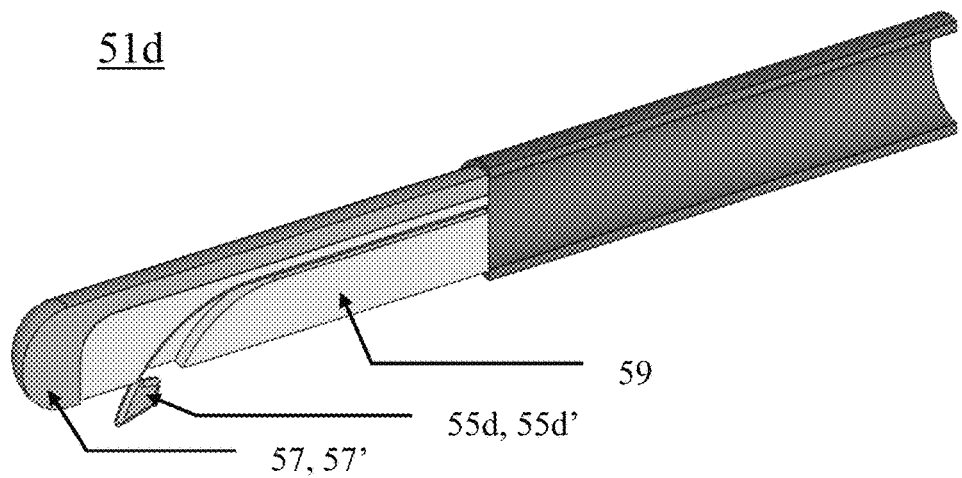
FIG. 9B depicts the tissue dissector of FIG. 9A with the blade shown in a projected position.

In the device of FIGS. 9A and 9B, the electrosurgical blade 55 comprises a flexible portion 55d that is constrained in the home position (see FIG. 9A). The flexible portion 55d is slidably positioned in an elongated slot 53a that is defined in the isolator 59. The flexible portion 55d is biased such that it causes the flexible portion 55d to project outward beyond the longitudinal profile of the distally directed member 57 (projected positioned shown in FIG. 9B) when the flexible portion 55d is released from the constraint in the home position (home position shown in FIG. 9A). The flexible portion 55d may be biased outward by a spring (not shown), for example.

A fourth embodiment of the technology shown in FIGS. 10A-10C takes the form of a combination device 60 that includes a tissue sealer and a dissector. The dissector has two operable dissecting arrangements based on the position of the jaws 62a and 62b (referred to collectively as jaws 62) and the blade 64. An isolating layer 63 is defined on both jaws 62.

The device 60 includes at least three electrodes, i.e., two electrosurgical jaws 62a and 62b and an electrosurgical blade 66, which collectively are configured to be able to operate in tissue sealing and tissue dissecting modalities. Accordingly, the device 60 includes at least three electrodes (i.e., a first electrode 62a', a second electrode 62b', and a third electrode 64'), a pair of opposing jaws 62 (i.e., a first jaw 62a and a second jaw 62b), and a pivotable electrosurgical blade 64.

The first opposable jaw 62a comprises the first electrode 62a', the second opposable 62b jaw comprises the second electrode 62b', and the pivotable electrosurgical blade 64 comprises the third electrode 64'. The electrosurgical blade 64 is pivotably-attached to the second jaw 62b at a first end 66 and unattached at the second end 68. The first and second electrodes 62a' and 62b' are operable together as a bipolar electrode pair, and the first and second electrodes 62a' and 62b' are collectively operable as a single electrode that operates together with the third electrode 64' as a bipolar electrode pair.

The device 60 may be configured for tissue sealing by grasping a portion of tissue between the two opposable jaws 62. In a procedure or portion of a procedure that includes a tissue sealing event, the first and second jaws 62 are the operative as paired bipolar electrodes. Aspects of the mechanics and electrical dynamics of tissue sealing are described in other related patent applications: application Ser. No. 12/121,734 filed May 15, 2008; application Ser. No. 09/169,019 filed Oct. 8, 1998 now U.S. Pat. No. 6,123,701 issued Sep. 26, 2000; application Ser. No. 13/021,633 filed Feb. 4, 2011; application Ser. No. 13/096,912 filed Apr. 28, 2011; application Ser. No. 13/070,391 filed Mar. 23, 2011;

application Ser. No. 13/110,848 filed May 18, 2011; application Ser. No. 13/021,633 filed Feb. 4, 2011; application Ser. No. 12/907,646 filed Oct. 19, 2010, each of which are incorporated by reference herein in their entirety.

The electrosurgical device 60 of FIGS. 10A-10C is configured to dissect tissue in two ways, depending on the operating arrangement of the electrode assembly, i.e., depending on whether the opposing jaws 62 are in an open position or a closed position, and depending on the position of electrosurgical blade 64 relative to the jaws 62. A first operable arrangement and a second operable arrangement of the electrode assembly are summarized below.

In the first operational arrangement of the device 60, the electrode assembly is arranged to kinetically dissect tissue with the jaws open, and the electrosurgical blade 64 is positioned between the jaws 62. The term 'kinetic dissection' refers to dissection that is driven by manual movement of the electrode assembly, or the device 60 as a whole, by the operator. Thus, the operational arrangement includes positioning the first and second jaws 62 in an open position (see FIG. 10A) to form a distal-facing gap, and pivoting the electrosurgical blade 64 such that it is disposed across the gap 27, as shown in FIG. 10B, the unattached end 68 of the blade 64 being stabilized by engaging the first jaw 62a.

In some embodiments being configured for tissue dissecting comprises being configured for a kinetic or distally-advancing cutting with a bilaterally supported blade. Distally-advancing cutting relates to operator controlled movement of the electrode assembly. A bilaterally-supported blade includes stable support at the end of the blade that is pivotably attached to the second jaw 62b, and stabilization or retention of the free end of the blade within the gap formed between the open jaws. When the jaws of the electrode assembly are in an open position, the height 'h' (see FIG. 10B) of the gap formed at the distal end of the jaws 62 comprises a tissue window; this height 'h' represents a limit to the thickness of a tissue portion that may be dissected by the device.

In the second operating arrangement of the device 60, the electrode assembly is arranged to kinetically dissect tissue with the jaws 62 closed or substantially closed, as shown in FIG. 10C, but with the electrosurgical blade 64 projected at an angle external to the second jaw 62b to which it is attached, and opposite the first jaw 62a. In some embodiments, being configured for tissue dissecting comprises locking or stabilizing the blade 64 at an acute angle 'a' with respect to the second jaw 62b, thereby enabling the trapping of tissue when the device 60 is being advanced in the direction of the acute angle 'a.' In another operable arrangement, being configured for tissue dissecting comprises locking the blade 64 at a substantially right angle with respect to the second jaw 62b, thereby enabling a tissue cutting profile of the blade's maximal depth.

In some embodiments, being configured for operator-driven movement of the electrode assembly comprises being configured to dissect tissue in accordance with any of distally directed translational movement, proximally directed translational movement, or lateral movement.

In some embodiments, being configured for tissue dissecting comprises being configured for cutting with a unilaterally supported blade. And, in some embodiments, tissue dissecting comprises operator driven movement cutting that cuts a portion of tissue that is limited by a length of the blade.

According to another aspect of the invention, the device 60, which combines tissue dissection and tissue sealing capability, includes an electrode assembly that includes: a pair of opposable jaws 62, a first jaw 62a and a second jaw 62b, wherein the first and second jaws 62 are rotationally joined at their respective proximal ends 70 such that the jaws 62 may pivot between an open position and a closed position, the open position creating a gap 27 between the two jaws 62; and a pivotable electrosurgical blade 64 rotationally joined to the second jaw 62b, the blade 64 pivotably configured to be stabilized in a first, second, and third position.

In a first position, the blade 64 (see FIG. 10A) is stowed within a profile of the second jaw 62a, the blade 64 being pivotable in either direction from the stowed position within an arc disposed between a second position (see FIG. 10B) that places a distal end 68 of the blade across the gap 27 between jaws 62 when they are in an open position such that the blade 64 is bilaterally supported, and a third position (see FIG. 10C) that places the distal end 68 of the blade 64 external to the second jaw 62a. In this embodiment of the device 60, the first and second electrode 62a' and 62b' are operable together as a bipolar electrode pair, and the first and second electrode 62a' and 62b' are collectively operable as a single electrode that operates together with the third electrode 64' as a bipolar electrode pair.

Several operational arrangements of the electrode assembly of the device 60 can be made, each being associated with a particular electrosurgical modality, as will be described hereinafter.

(1) When the jaws 62 are in an open position and when the electrosurgical blade 64 is in the parked position, the gap 27 between the first and second jaws 62 allows positioning of the first and second electrodes 62a' and 62b' such that they are configured to perform sealing of tissue portions that may be captured within the jaws 62.

(2) When the jaws 62 are in an open position and when the electrosurgical blade 64 is in the second position, the first and third electrode 62a' and 64' are positioned to perform distally advancing tissue dissection by the blade 64 as it is supported bilaterally.

(3) When the jaws 62 are in a closed position, and when the blade is pivotably positioned external to the second jaw 62b, the second and third electrodes 62b' and 64' are positioned to perform operator-movement driven tissue dissection by blade as it is unilaterally supported.

The device 60 further comprises an isolator layer 63 separating first and second electrodes 62a' and 62b' when the blade 64 is in the second position of FIG. 10B, and an isolator layer 63 separating the second and third electrodes 62b' and 64'. The device 60 may further comprise a mechanical blade disposed proximal to the electrode assembly and configured to be distally advanceable through tissue after the first and second electrodes 62a' and 62b' have effected a sealing of the tissue. Finally, in some embodiments of the device 60, being configured for tissue sealing comprises being configured to grasp a portion of tissue between the two opposable jaws 62.

According to one exemplary method of using the device of FIGS. 3-5, the method comprises engaging a portion of a tissue sheet within the distal facing tissue trap; and delivering sufficient RF energy from the tissue dissection trap to the engaged portion of tissue such that the portion of tissue is dissected. Some embodiments of this method may further include manually advancing the electrode assembly in the direction of a targeted dissection line; and delivering RF energy while advancing. In methods that include the operation of devices equipped with an electrode assembly such as that of FIGS. 3-5, the method may further comprise adjusting the angle of the jaws, and it may further include stabilizing the angle of the jaws.

Although the jaws 36 of FIG. 4 may not be as heavy or robust as those of FIGS. 10A-10C in terms of being able to deliver compressive forces associated with tissue sealing, in some embodiments, the jaws 36 are configured to grasp tissue with sufficient force that the tissue is stabilized within the jaws 36. Accordingly, these embodiments are capable of a stabilized dissection as well as kinetic dissection.

Embodiments of the provided technology include methods of using devices of FIGS. 6A-9B, as summarized above. The method comprises providing a bipolar electrode assembly per device; positioning the electrosurgical blade such that it projects beyond the longitudinal profile of the distally directed member; advancing the bipolar electrode assembly into a tissue sheet so as to engage a portion of the tissue sheet, the first and second jaws of the electrode assembly in an open position, forming a distally-directed tissue dissection trap; and delivering sufficient RF energy from the tissue dissection trap to the engaged portion of tissue such that the portion of tissue is dissected.

In some embodiments of this electrosurgical dissection method, the advancing of the electrode assembly and delivering energy steps are performed simultaneously or in at least partially overlapping fashion. And in some embodiments, the tissue dissection trap remains in an open position continuously or substantially continuously while engaging the portion of the tissue sheet.

In a method of electrosurgical dissection that involves the use of the devices of FIGS. 6A-9B, the method comprises moving a bipolar electrode assembly across a target tissue such that the electrosurgical blade, when projecting outward, dissects a portion of tissue to a controlled depth, such movement comprising movement in any of three directions, a distal direction, a proximal direction, or a lateral direction.

With regard to a method of electrosurgery involving the use of the devices of FIGS. 10A-10C, the method comprises passing a bipolar electrode assembly into an operating space; performing at least two electrosurgical procedures with the bipolar electrode assembly in the operating space prior to removing it from the operating space, a first procedure comprising tissue dissecting and a second procedure comprising tissue sealing, wherein the two procedures may be performed in any order; and upon completing the electrosurgical procedures, removing the bipolar electrode assembly from the operating space. The operating space for embodiments of these dual purpose devices may be within a laparoscopic environment or in an open environment. In the case of a laparoscopic space, the use of a device able to perform both tissue sealing and tissue dissecting is particularly advantageous in that it allows both procedures to be done within the temporal context between a single entry and exit of the device through a trocar.

In some embodiments of this method, making use of the devices of FIGS. 10A-10C, electrosurgical dissecting comprises moving an electrosurgical assembly along a line of dissection and delivering energy simultaneously. In typical embodiments of the method, performing two electrosurgical procedures comprises delivering RF energy in association with each procedure. In some of the embodiments of the electrosurgical method, tissue dissecting comprises dissecting a plurality of tissue dissecting sites. In some of the embodiments of the electrosurgical method, tissue sealing comprises sealing a plurality of tissue sealing sites.

With regard to electrosurgical tissue sealing with the device 60 of FIGS. 10A-10C, the embodiments of method may comprise compressing a target tissue sealing site and delivering RF energy to the sealing site. In this operational arrangement, the blade is disposed in a home position or a neutral position, such that it does not project beyond the profile of the jaws.

With regard to electrosurgical tissue dissecting device according to the device 60 of FIGS. 10A-10C, embodiments of the method may comprise distally advancing a bilaterally supported blade, the blade pivotably positioned across a gap between the open jaws.

Further with regard to electrosurgical dissecting, embodiments of the method may comprise cutting through a portion of a tissue sheet along a line of dissection. With regard to these embodiments, wherein along the line of dissection, the tissue sheet has a thickness no greater than a height of a cutting window of the bipolar electrode assembly, such cutting window being limited at least by the height of a gap between the distal tips of the opposing jaws when the jaws are in an open position.

With regard to electrosurgical dissecting, embodiments of the method may comprise dissecting with the electrosurgical blade when it is positioned external to the second jaw, projecting at an angle. In such an arrangement, the blade is unilaterally supported at the point of its pivotable attachment to the second jaw.

Embodiments of this method electrosurgical dissecting may include moving an electrosurgical cutting blade through a surface aspect of a tissue portion in any of three directions, a distal direction, a proximal direction, or a lateral direction. Embodiments may further include cutting a line of dissection into a portion of a tissue to a controlled depth.

Embodiments of the provided technology include devices and systems that incorporate embodiments of the electrode assemblies as summarized above. Devices thus may include any of the described electrode assemblies; a shaft supporting the electrode assembly; and a hand piece supporting the shaft. Embodiments may further include a rotational mechanism configured to rotate the shaft and the electrode assembly with respect to the hand piece, and/or they may include an articulating assembly disposed between the electrode assembly and the shaft. The scope of each embodiment described or depicted should be understood to include technology features described or depicted in the context of any other particular embodiment.

Some device and electrode assembly embodiments are sized and configured to be able to enter and operate in a laparoscopic space through currently available commercial trocars, including 5 mm diameter trocars. In these particular embodiments, therefore, both the shaft and the electrode assembly (in a closed state or arrangement) are of a sufficiently narrow diameter that they can easily pass through a 5 mm trocar.

Systems as provided by the technology may include any of described or depicted devices, as well as a generator operably connected to the electrosurgical device. Some embodiments of the generator are operable to deliver RF energy to the electrodes in any waveform selected from the group comprising a continuous cutting RF voltage waveform, a blended waveform with a continuous RF voltage waveform with a duty cycle of less than 100%, and a coagulation waveform comprising pulsed RF voltage. Further details of energy delivery capability are shown in Table 1.

Electrical Algorithm Parameters: Energy Delivery Ranges

Table 1 provides example ranges of operating parameters for the electrosurgical tissue sealing and the electrosurgical tissue dissecting operating modalities of embodiments of the technology. Embodiments of systems that are dedicated to dissecting are enabled to deliver energy within the parameters of dissecting energy. Embodiments of systems with electrode assemblies that are configured for dual purposes of both sealing and dissecting are enabled to deliver energy consistent with the parameters for both tissue sealing and tissue dissection.

TABLE 1

Electrical Algorithm Parameters: Energy Delivery Ranges

| Parameter | Sealing | Dissecting |
|---|---|---|
| Max Voltage (volts) | 85-115 volts | 400 volts |
| Ramp End Power (watts) | 150 watts | 10-100 watts |
| Ramp Rate (watts/sec) | 50-150 watts/sec | 255 watts/sec |

What is claimed:

1. An electrosurgical tissue dissecting device comprising:
a shaft;
a distally directed member that extends in a distal direction from the shaft;
a first electrode that either forms part of or is positioned on the distally directed member; and
an electrosurgical blade which is a second electrode that is configured to pivot with respect to the first electrode, wherein a proximal end of the electrosurgical blade is pivotably mounted to the distally directed member, and is movable such that at least a portion of the blade is exposed, wherein a distal end of the second electrode is configured to pivot with respect to the first electrode about a pivot point that is defined at the proximal end of the second electrode, and
wherein the distally directed member defines an elongated recess formed on a surface of the distally directed member, wherein the electrosurgical blade is pivotable with respect to the distally directed member to a position in which the electrosurgical blade is disposed entirely within the recess.

2. The electrosurgical tissue dissecting device of claim 1, wherein the electrosurgical blade is pivotable with respect to the distally directed member between a home position, in which the electrosurgical blade is longitudinally aligned with the distally directed member, and an outwardly projected position, in which the electrosurgical blade projects beyond the longitudinal profile of the distally directed member.

3. The electrosurgical tissue dissecting device of claim 2, wherein the electrosurgical blade defines a cutting zone depth when the electrosurgical blade is positioned in the outwardly projected position.

4. The electrosurgical tissue dissecting device of claim 3, wherein the cutting zone depth is controllable by pivoting the distal end of the second electrode with respect to the first electrode to change a distance that the electrosurgical blade projects from the device.

5. The electrosurgical tissue dissecting device of claim 1, wherein the electrosurgical blade is pivotable with respect to the distally directed member through a pivot arc range.

6. The electrosurgical tissue dissecting device of claim 5, wherein the pivot arc range is about 90 degrees.

7. The electrosurgical tissue dissecting device of claim 5, wherein the electrosurgical blade is lockable at any position within the pivot arc range.

8. An electrosurgical tissue dissecting device comprising:
a shaft;
a distally directed member that extends in a distal direction from the shaft;
a first electrode that either forms part of or is positioned on the distally directed member; and
an electrosurgical blade which is a second electrode that is movable with respect to the first electrode,
wherein the electrosurgical blade is movable with respect to the distally directed member such that at least a portion of the electrosurgical blade is exposed,
wherein the electrosurgical blade is movable with respect to the distally directed member between a home position, in which the electrosurgical blade is positioned within a longitudinal profile of the distally directed member, and an outwardly projected position, in which the electrosurgical blade projects beyond the longitudinal profile of the distally directed member, and
wherein the electrosurgical blade comprises a flexible portion that is slidably positioned in an elongated slot, the electrosurgical tissue dissecting device further comprising an isolator that isolates the first electrode from the second electrode to prevent electrical contact between the first electrode and the second electrode, wherein the elongated slot is defined in the isolator.

9. The electrosurgical tissue dissecting device of claim 8, wherein the electrosurgical blade defines a cutting zone depth when the electrosurgical blade is positioned in the outwardly projected position.

10. The electrosurgical tissue dissecting device of claim 8, wherein the flexible portion is constrained in the home position.

11. The electrosurgical tissue dissecting device of claim 8, wherein the flexible portion is biased toward the outwardly projected position.

12. The electrosurgical tissue dissecting device of claim 8, wherein the flexible portion is releasable from the home position to permit the flexible portion to move to the outwardly projected position.

* * * * *